(12) United States Patent
Taguchi et al.

(10) Patent No.: US 6,661,912 B1
(45) Date of Patent: Dec. 9, 2003

(54) INSPECTING METHOD AND APPARATUS FOR REPEATED MICRO-MINIATURE PATTERNS

(75) Inventors: Junichi Taguchi, Kodama-gun (JP); Aritoshi Sugimoto, Bunkyo-ku (JP); Masami Ikota, Higashiyamato (JP); Yuko Inoue, Okegawa (JP); Tetsuya Watanabe, Honjo (JP); Wakana Shinke, Hamura (JP)

(73) Assignee: Hitachi Electronics Engineering Co., Ltd., Tokyo (JP)

( * ) Notice: Subject to any disclaimer, the term of this patent is extended or adjusted under 35 U.S.C. 154(b) by 0 days.

(21) Appl. No.: 09/127,960

(22) Filed: Aug. 3, 1998

(51) Int. Cl.$^7$ .................................................. G06K 9/00
(52) U.S. Cl. ..................................... 382/145; 356/237.2
(58) Field of Search ............................... 382/141, 145, 382/147, 148, 149; 348/87, 126; 356/237.3, 237.4, 237.5, 237.2; 250/559.04, 559.41, 559.42, 559.43, 559.44, 559.46, 559.45, 559.05, 559.06, 559.08, 559.39, 559.4; 438/16; 702/40, 82, 172, 459

(56) References Cited

U.S. PATENT DOCUMENTS

| 4,449,818 A | * | 5/1984 | Yamaguchi et al. | ...... 356/237.3 |
| 5,544,256 A | * | 8/1996 | Brecher et al. | .............. 382/149 |
| 5,822,055 A | * | 10/1998 | Tsai et al. | ................ 356/237.1 |
| 5,917,588 A | * | 6/1999 | Addigo | ..................... 356/237.2 |
| 6,288,780 B1 | * | 9/2001 | Fairely et al. | ........... 356/237.1 |

\* cited by examiner

Primary Examiner—Samir Ahmed
(74) Attorney, Agent, or Firm—Antonelli, Terry, Stout & Kraus, LLP

(57) ABSTRACT

An apparatus for inspecting foreign matter in repeated micro-miniature patterns formed upon a surface of an object to be inspected, comprising: an inspection light illuminating device for irradiating an inspection light directed upon the surface of the object to be inspected, on which the repeated micro-miniature patterns are formed; a scattered light detector for detecting scattered light of the inspection light being scattered upon the surface said object to be inspected; means for obtaining a first information related to a foreign matter attaching upon the surface of said object to be inspected, which is obtained on a basis of the detection of said scattered light by said scattered light detector; an illumination means for applying a bright field illumination upon the surface of the object to be inspected, on which the repeated micro-miniature patterns are formed; means for picking up the image of the foreign matter, under a bright field illumination by said illumination means; means for obtaining a second information related to said foreign matter, depending upon an image of said foreign matter, which is obtained on a basis of said picking up of the image by said image picking up means under the bright field illumination; and means for displaying said first information and said second information, both being related to said foreign matter, on a display screen thereof.

12 Claims, 18 Drawing Sheets

FIG. 3(a)  FIG. 3(b)  FIG. 3(c)
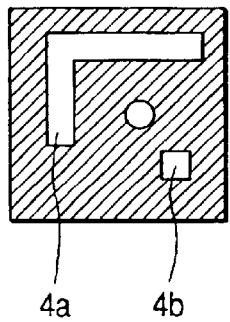
4a  4b
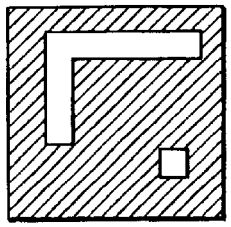
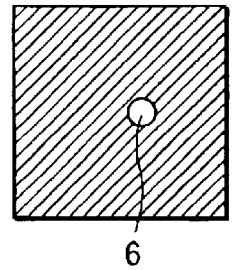
6
FIG. 3(d)
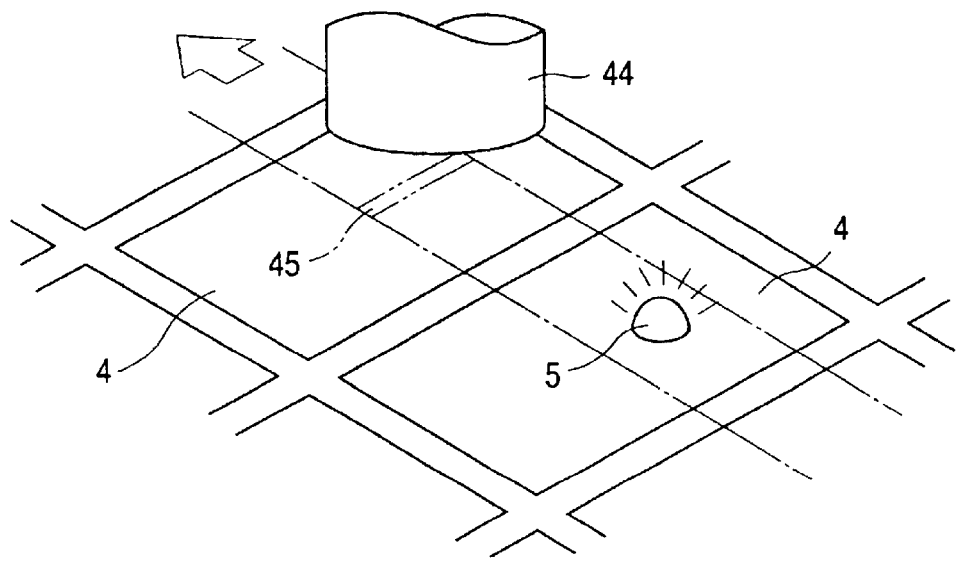

FIG. 5(a)
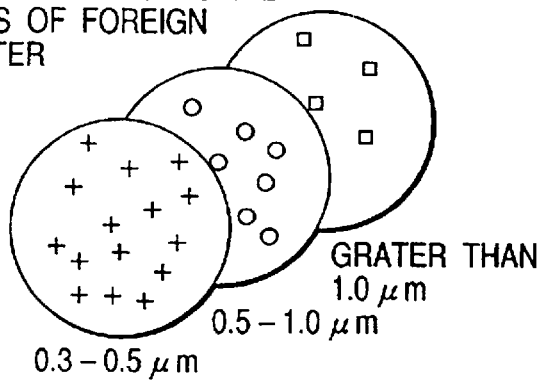
MAPS FOR RESPECTIVE SIZES OF FOREIGN MATTER

GRATER THAN 1.0 μm
0.5 – 1.0 μm
0.3 – 0.5 μm

FIG. 5(b)
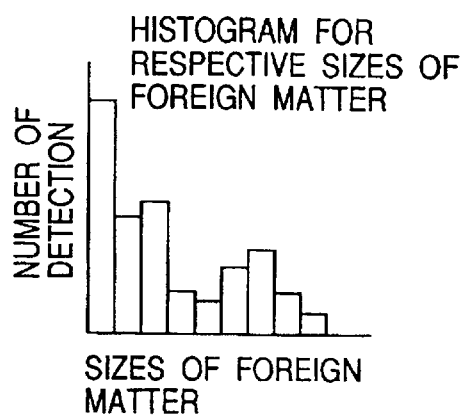
HISTOGRAM FOR RESPECTIVE SIZES OF FOREIGN MATTER

NUMBER OF DETECTION

SIZES OF FOREIGN MATTER

FIG. 5(c)
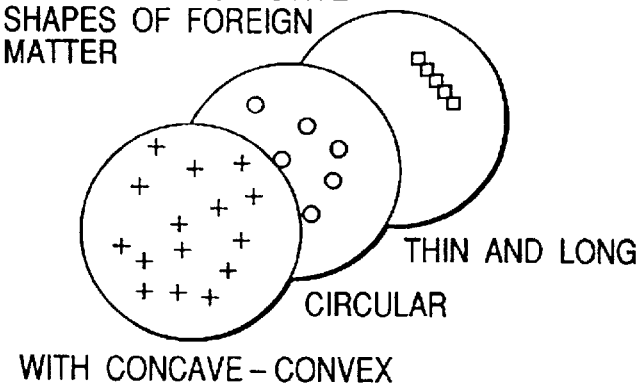
MAPS FOR RESPECTIVE SHAPES OF FOREIGN MATTER

THIN AND LONG
CIRCULAR
WITH CONCAVE – CONVEX

FIG. 5(d)
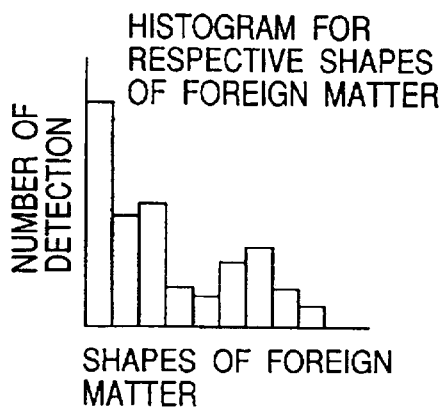
HISTOGRAM FOR RESPECTIVE SHAPES OF FOREIGN MATTER

NUMBER OF DETECTION

SHAPES OF FOREIGN MATTER

FIG. 5(e)
GRAPH OF RESULT OF INSPECTION IN TIME SEQUENCE

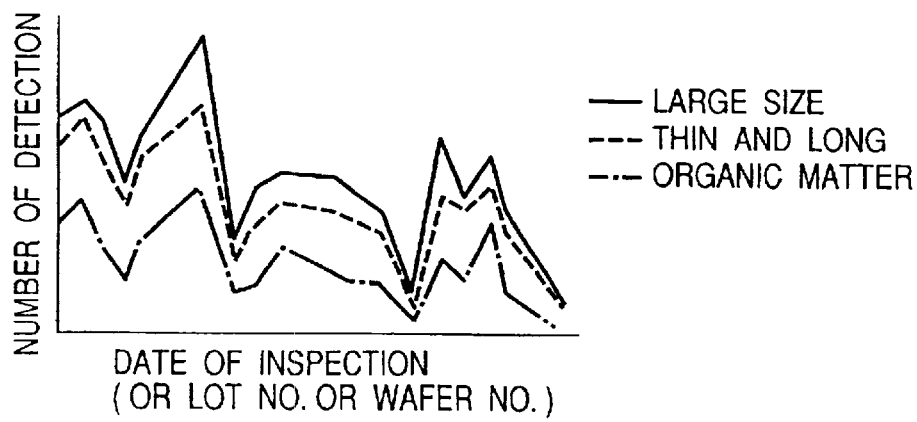

NUMBER OF DETECTION

—— LARGE SIZE
--- THIN AND LONG
—·— ORGANIC MATTER

DATE OF INSPECTION
(OR LOT NO. OR WAFER NO.)

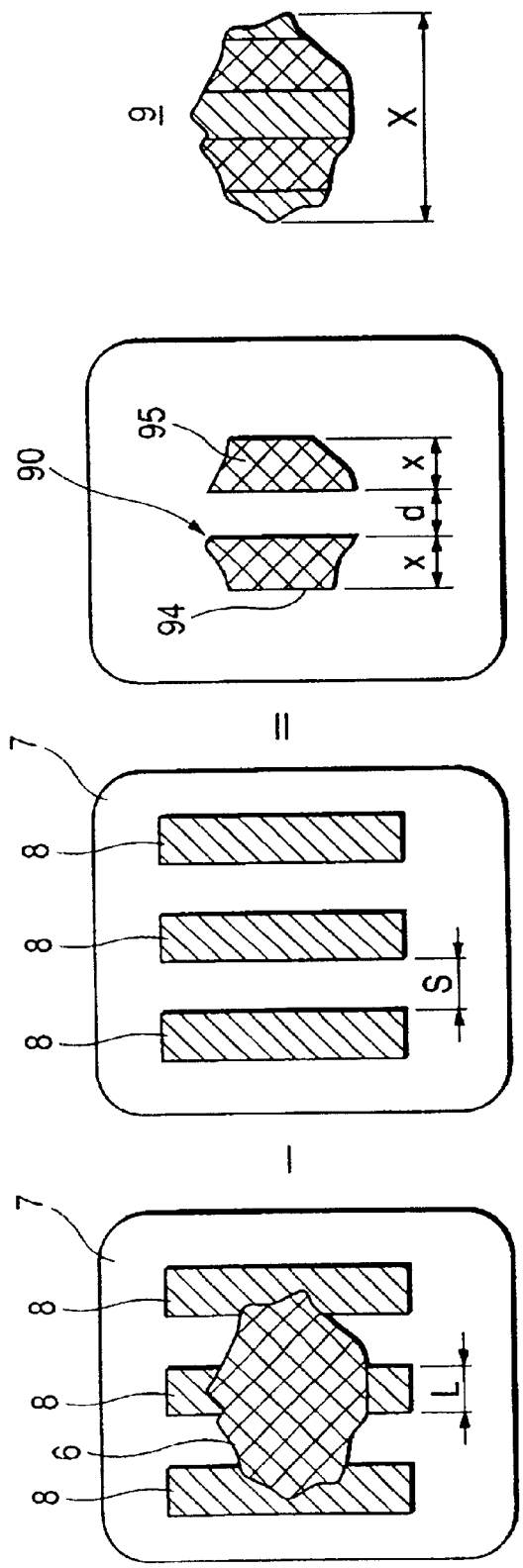

▨ KILLER DEFECT CHIP
(OMITTED ILLUSTRATION OF DETECTED FOREIGN MATTER)

▧ POSSIBLE DEFECT CHIP
(OMITTED ILLUSTRATION OF DETECTED FOREIGN MATTER)

☐ GOOD CHIP

● DETECTED FOREIGN MATTER

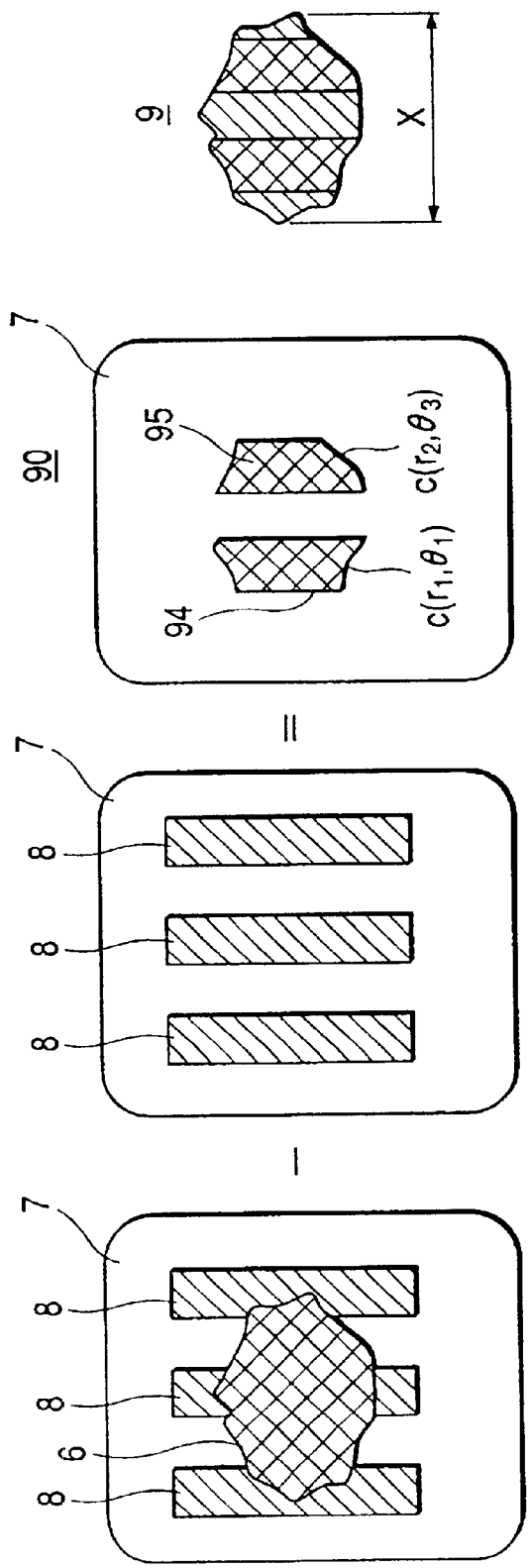

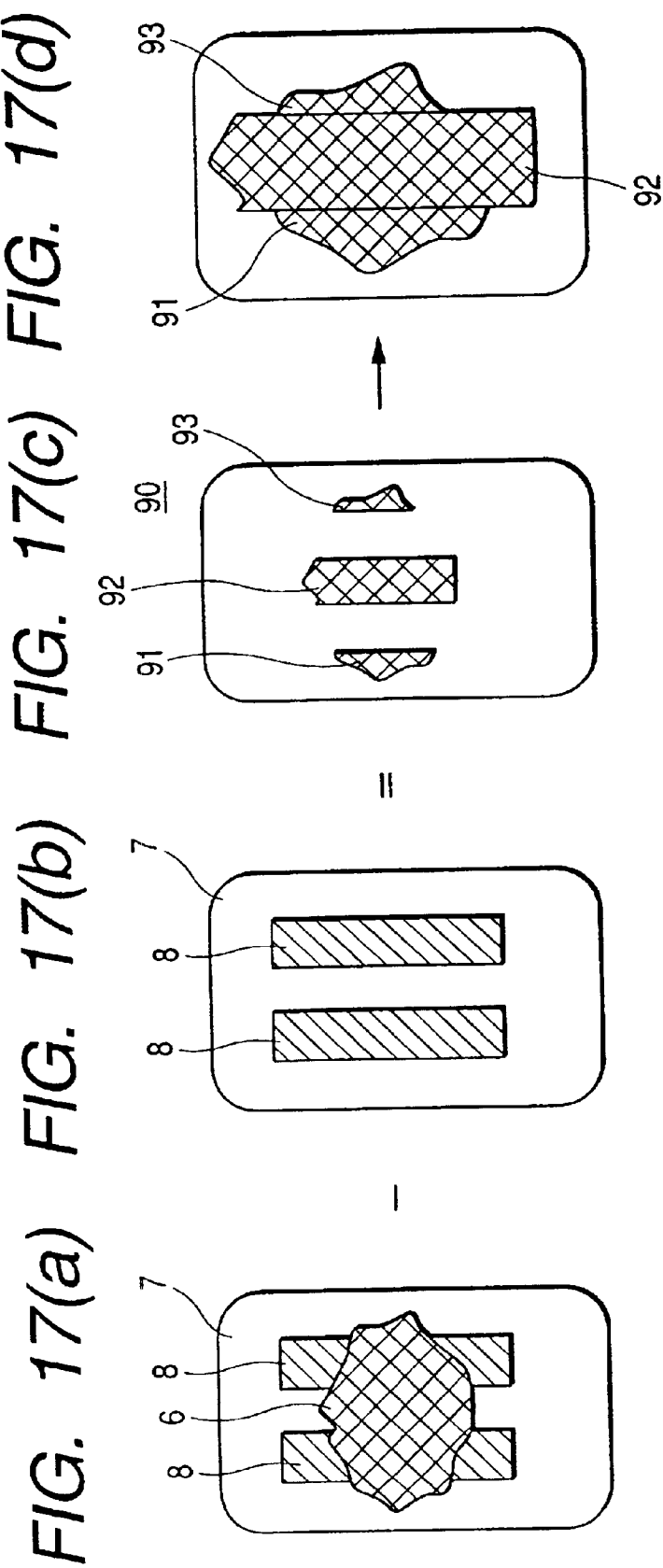

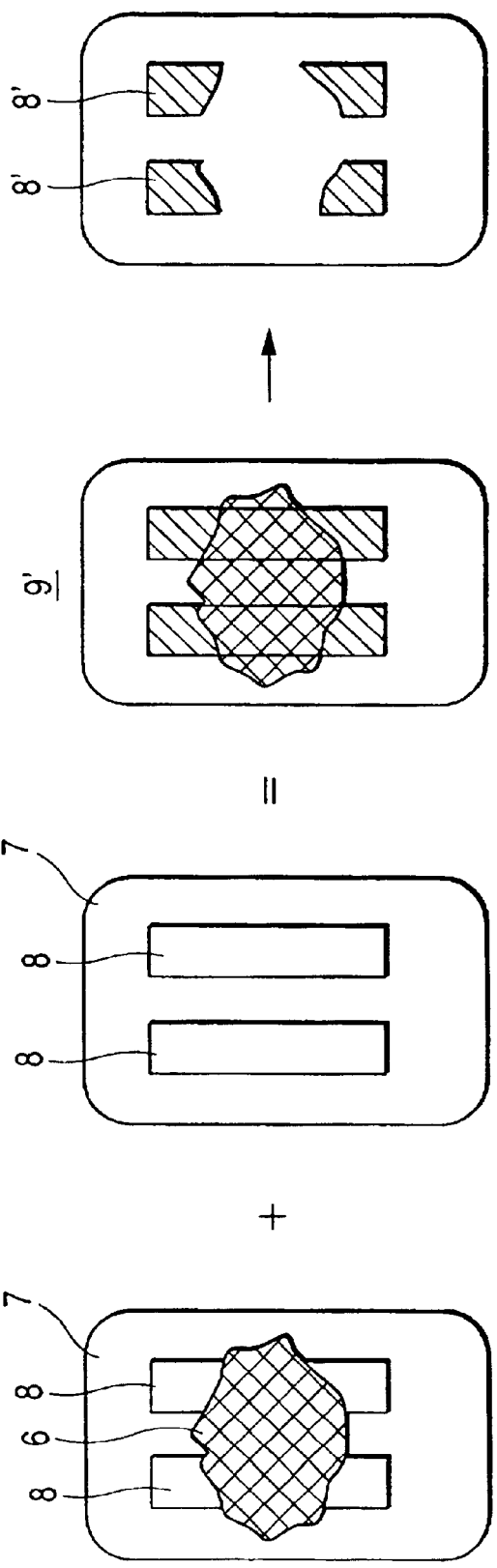

INSPECTING METHOD AND APPARATUS FOR REPEATED MICRO-MINIATURE PATTERNS

BACKGROUND OF THE INVENTION

1. Field of the Invention

The present invention relates to a method and an apparatus for inspecting foreign matters in or on repeated micro-miniature patterns, in particular, to the method and the apparatus for use in inspecting or detecting minute or microscopic foreign matter(s) upon a surface of an object to be inspected, such as the repeated micro-miniature patterns which are formed on a semiconductor wafer, with high sensitivity.

2. Description of Related Art

With great advance in scale of integration and in miniaturization of circuitry patterns of a semiconductor integrated circuit (herein after, it is called only by "IC") in recent years, circuit patterns being formed on it come to be in an order of 1 $\mu$m or less than that in width thereof. For producing such an IC with high productivity, it is necessary to detect particles or foreign matters attached on the surface of the wafer and to inspect or examine sizes, shape, feature and property thereof, so as to quantitatively obtain cleaning degrees in various apparatuses and/or processes for producing the semiconductor, and thereby to manage production process appropriately. Therefore, conventionally, the detection and/or inspection of the foreign matters on wafers was applied to, with methods and/or apparatuses for inspection of foreign matters attached or adhered to the wafers, as works in IC production facilities in factories, so as to manage the production processes appropriately.

The conventional inspection apparatuses for inspection of foreign matters on wafers can be divided roughly into two categories. A first one is a patterned wafer inspection apparatus of an image comparison type (hereinafter, it is called by a "visual inspection apparatus"), in which the comparison is carried out between the image under a bright field of an illumination and a reference pattern which is previously stored. A second one is a patterned wafer inspection apparatus of such type (hereinafter, it is called by "an inspection apparatus") that it detects scattered light in a dark field under an inclined illumination, acknowledges existence of defects or foreign matters, and determines coordinate positions and the number thereof, by means of the coordinates obtained at the time of detection of the scattered light.

Further, an example of such apparatuses for inspection of defects on the wafers is described on pages from 97 to 116 of "Nikkei Micro-devices, March, 1997", which is published by Nikkei Business Publication, Inc.

The visual inspection apparatus mentioned above has an advantage that it shows high accuracy in inspection; however, it has drawbacks that throughput thereof is low and that it is expensive in price. And, since an image or visual data can be obtained by the visual inspection apparatus, it enables a so-called review (i.e., a confirmation or an inspection by means of the image, visually). However, by the inventors of the present invention, it is made clear that, in the visual inspection apparatus, information not only necessary but also unnecessary to be reviewed are also provided too much, in comparison with the number of pieces of the wafers to be inspected, including such as for a microscopic defect, therefore, a probability of obtaining fatal or killer defects is very low and there is a drawback that an efficiency of the review comes to be low.

On the contrary, though the inspection apparatus mentioned above has a drawback that it is lower than that of the visual inspection apparatus in the accuracy, it has an advantages that the throughput of it is higher, comparing to that of the visual inspection apparatus, and that it is also lower in the price thereof. And, since the data which can be obtained from the inspection apparatus includes only the coordinate positions of the defects in a surface area of the wafer, as well as an intensity of the scattered light, therefore, it is impossible to obtain information relating to the size(s) of the defect (i.e., a diameter of the particle) and the shape thereof (even if possible, within a degree to classify it into S (small), M (medium) and L (large) in the size, roughly). Accordingly, for obtaining the information concerning to those in more detail, there is a necessity of using the inspecting apparatus of analyzer type, such as the visual inspection apparatus as mentioned above or an another kind of inspection apparatus, such as a SEM (Scanning Electron Microscope) which, however, takes a long time for inspection or analysis and expensive in the price.

SUMMARY OF THE INVENTION

An object, according to the present invention, is to provide a method and an apparatus for inspecting foreign matters, which can obtain such the fatal defects with a good efficiency, and is also able to inspect the sizes and the shapes thereof.

According to the present invention, for achieving the object mentioned in the above, first of all, there is provided a method for inspecting foreign matter in repeated micro-miniature patterns formed upon a surface of an object to be inspected, comprising following steps:

irradiating an inspection light directed upon the surface of the object to be inspected, on which the repeated micro-miniature patterns are formed, with an inspection light irradiating device;

detecting scattered light of the inspection light being scattered upon the surface of said object to be inspected with a scattered light detector;

determining a coordinate position of a foreign matter upon the surface of said object to be inspected, on a basis of the detection of said scattered light in the above step;

picking up an image of said foreign matter which is determined with the coordinate position thereof, under a bright field illumination by an irradiation means, at a coordinate position which is corresponding to that in said scattered light detecting step; and deciding said foreign matter at least one of in size, shape, color and property thereof, depending upon an image of said foreign matter which is extracted on a basis of said picking up of the image obtained in the above step.

Further, according to the present invention, for achieving the object mentioned in the above, there is provided an apparatus for inspecting foreign matter in repeated micro-miniature patterns formed upon a surface of an object to be inspected, comprising:

an inspection light irradiating device for irradiating an inspection light directed upon the surface of the object to be inspected, on which the repeated micro-miniature patterns are formed;

a scattered light detector for detecting scattered light of the inspection light being scattered upon the surface said object to be inspected;

means for determining a coordinate position of a foreign matter upon the surface of said object to be inspected, on a basis of the detection of said scattered light;

an irradiation means for applying a bright field illumination upon the surface of the object to be inspected, on which the repeated micro-miniature patterns are formed;

means for picking up an image of the foreign matter which is determined with the coordinate position thereof, under a bright field illumination by said irradiation means, at the coordinate position which corresponding to that which is determined by said coordinate position identifying means; and means for deciding the foreign matter at least one of in size, shape, color and property thereof, depending upon an image of the foreign matter which is extracted on a basis of said picking up of the image obtained by said image picking up means.

And, further according to the present invention, there is also provided an apparatus for inspecting foreign matter, as defined in the above, further including:

means for obtaining a reference image by picking up the image of the micro-miniature pattern, under a bright field illumination, at an another coordinate position on the surface of said object to be inspected, which is corresponding to but different from the coordinate position which is determined by said determining means; and means for obtaining an arithmetic process image between said object image and said reference image, wherein said decision means decide a presence of a defect at the determined coordinate position on said object to be inspected, which is previously designated, on a basis of the arithmetic process image obtained by said arithmetic process image obtaining means.

Furthermore, according to the present invention, for achieving also the object mentioned in the above, there is provided an apparatus for inspecting foreign matter in repeated micro-miniature patterns formed upon a surface of an object to be inspected, comprising:

an inspection light irradiating device for irradiating an inspection light directed upon the surface of the object to be inspected, on which the repeated micro-miniature patterns are formed;

a scattered light detector for detecting scattered light of the inspection light being scattered upon the surface said object to be inspected;

means for obtaining a first information related to a foreign matter attaching upon the surface of said object to be inspected, which is obtained on a basis of the detection of said scattered light by said scattered light detector;

an irradiation means for applying a bright field illumination upon the surface of the object to be inspected, on which the repeated micro-miniature patterns are formed;

means for picking up an image of said foreign matter, under a bright field illumination by said irradiation means;

means for obtaining a second information related to said foreign matter depending upon the image of the foreign matter, which is obtained on a basis of said picking up of the image by said image picking up means under the bright field illumination; and means for displaying said first information and said second information on a display screen thereof.

And, according to the present invention, for also achieving the above-mentioned object, there is provided a method for inspecting foreign matter in repeated micro-miniature patterns formed upon a surface of an object to be inspected, comprising following steps:

obtaining an object image by picking up the image of the micro-miniature pattern, under a bright field illumination, at a coordinate position on the surface of said object to be inspected, which is designated previously;

obtaining a reference image by picking up the image of the micro-miniature pattern, under a bright field illumination, at an another coordinate position on the surface of said object to be inspected, which is different from but corresponding to said coordinate position mentioned in the above step;

obtaining an arithmetic process image between said object image and said reference image; and deciding of a presence of a foreign matter at the coordinate position on said object to be inspected, which is previously designated, on a basis of a condition of said arithmetic process image obtained in the above step.

Further other objects and/or features of the present invention will be clear from detailed description of preferred embodiments and attached drawings, the brief explanation of which will be given below.

BRIEF DESCRIPTION OF DRAWINGS

FIGS. 3(*a*) through (*d*) show extracting functions of an object image, in particular, (a) an image in a condition that foreign matter is adhered, (b) an image in a condition that no foreign matter is adhered, (c) an foreign matter image which is extracted, and (d) a perspective view of a condition that the image is picked up;

FIGS. 5(*a*) through (*e*) are explanatory views of showing various analysis data, such as, (a) maps for respective sizes of the foreign matters, (b) a histogram for respective sizes of the foreign matters, (c) maps for respective shapes of the foreign matters, (d) a histogram for respective shapes of the foreign matters, and (e) a graph for showing a result of analysis in a time sequence;

FIGS. 13(a) through (d) show views for explaining an acknowledgment of a single foreign matter when the image is divided into two (2) in the foreign matter detecting method, according to the another embodiment of the present invention mentioned in the above;

FIGS. 16(a) through (d) show views for explaining an acknowledgment of a single foreign matter, when an image is divided into two (2) in the first variation of the another embodiment of the present invention mentioned in the above;

FIGS. 17(a) through (d) show views for explaining an acknowledgment of a single foreign matter, in a second variation of the another embodiment of the present invention mentioned in the above; and FIGS. 18(a) through (d) show views for explaining an acknowledgment of a single foreign matter, in a third variation of the another embodiment of the present invention mentioned in the above.

DESCRIPTION OF THE PREFERRED EMBODIMENTS

Hereinafter, detailed explanation of the embodiments according to the present invention will be given by referring to attached drawings, and in the following description, the word "foreign matter" is used, including, such as, defect in pattern shape, defect of pattern deficit, particle or contamination, residue and scratch on a surface of an object to be inspected.

Figure 1:
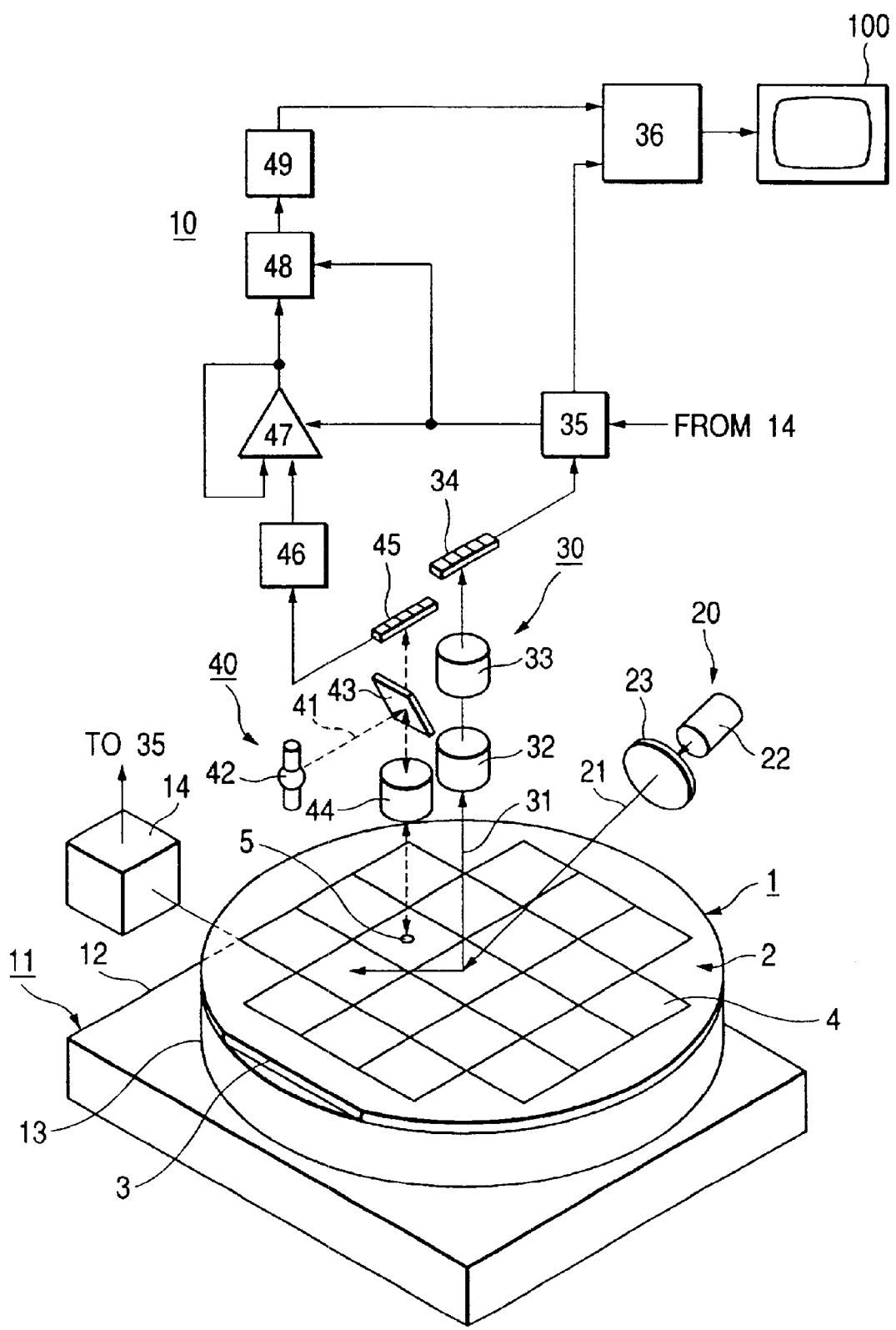
FIG. 1 shows a perspective view of an apparatus for detecting foreign matter in accordance with an embodiment of the present invention.
Figure 2:
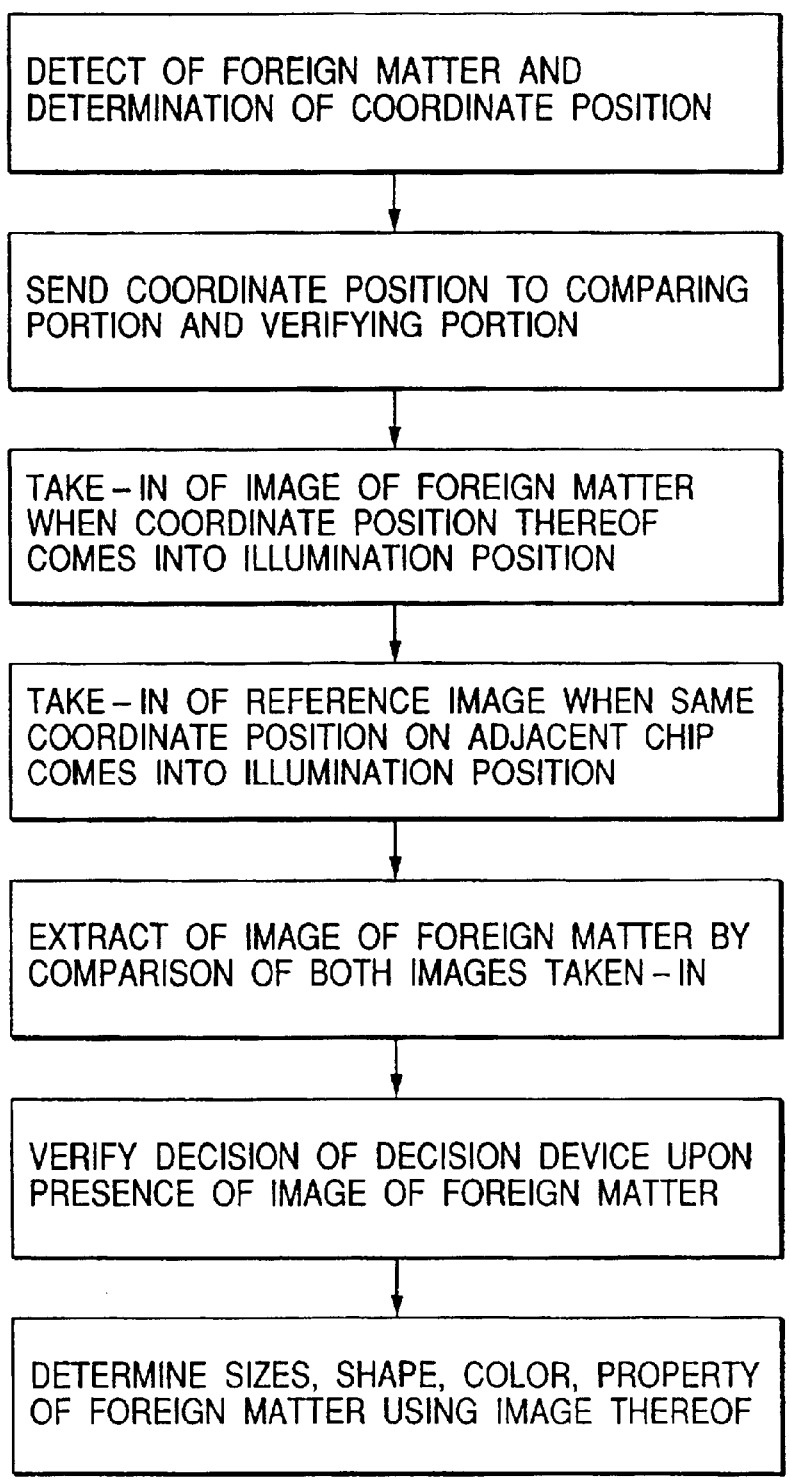
FIG. 2 shows a flow of a method for detecting foreign matter, being processed with use of the foreign matter detecting apparatus in accordance with the embodiment of the present invention.

FIG. 1 shows the perspective view of an apparatus for inspecting foreign matter(s) according to an embodiment of the present invention, FIG. 2 a flow chart for showing a method for the same, and FIGS. 3 through 5 an explanatory drawings for explaining the function thereof.

In the present embodiment, the apparatus for inspecting foreign matters according to the present invention is constructed of such type that the inspection apparatus 10 detects a scattered light from a wafer, as an object to be inspected, under a dark field with an inclined illumination, and it acknowledges presence, coordinate positions and the number of the foreign matter(s) from the coordinates at the time point when the scattered light is detected. The object to be inspected, i.e., a wafer 1 is in a process of manufacturing an IC, such as DRAM as an example, in every chip portion 4 on a first main surface 2 thereof, and the chip portions 4 are-regularly aligned in vertical and horizontal directions with respect to an orientation flat 3 which is formed by cutting a portion of the wafer 1. When a foreign matter 5 attaches or adheres upon the first main surface 2 of the wafer 1, it comes to be a cause of failure. Therefore, the foreign matter 5 attached on the first main surface 2 of the wafer 1 is detected by the inspection apparatus 10, and further it is inspected in the position, the number, sizes, shape, color and property thereof, thereby obtaining a degree of cleanness in apparatuses and processes for manufacturing various kinds of semiconductors, so as to manage the production process appropriately.

The inspection apparatus 10 comprises a stage device 11 which has a X-Y table 12 for scanning on the wafer 1 as the object 1 to be inspected, a θ table 13 for rotating the wafer 1 in θ direction, a focusing mechanism (not shown in figure) and a controller 14 for controlling those. And, for inspecting an entire surface of the wafer 1, the X·Y scanning of the wafer 1 is carried out by the stage device 11. During this scanning, an information of the coordinate position concerning the wafer 1, as the object to be inspected, is inputted from the controller 14 into a decision apparatus of the foreign matter which will be described in later, sequentially.

Obliquely upward the stage device 11, there is provided an inspection light illumination device 20. The inspection light illumination device 20 comprises a laser irradiation device 22 for irradiating a laser beam 21 upon the wafer 1 and a condenser lens 23 for condensing the laser beam 21, and it effects an inclined illumination upon the wafer 1 by irradiating the condensed laser beam 21 upon the wafer 1 as the object to be inspected, which is held on the stage device 11.

Directly above the stage device 11 is provided a scattered light detecting device 30. This scattered light detecting device 30 has an objective lens 32 for collecting the scattered lights 31 which are scattered upon the surface of the wafer 1, accompanying the inclined irradiation of the laser light 21 thereupon, a relay lens 33 for causing the scattered lights 31 to form an image on a light receiving surface, and a scattered light detector 34 for detecting the scattered lights on a basis of the image formed on the light receiving surface thereof. Namely, the scattered light detecting device 30 is so constructed that it detects the scattered lights 31 under a dark field illumination. In the present embodiment, the scattered light detector 34 is constructed with a line sensor, in which solid-state image sensor of photoelectric conversion type, such as CCD (Charge Coupled Device) are aligned in a line, along with a Y direction orthogonal to the direction of movement of the stage.

To the scattered light detector 34 is connected the foreign matter determining device 35. This foreign matter determining device 35 is so constructed that it decides the presence of the foreign matter upon the wafer 1 on the basis of the time point when detecting the scattered light from the scattered light detector 34, and it identifies or determines the coordinate position of the foreign matter by referring the data which is decided to a coordinate position data from the controller 14 of the stage device 11. Also, the scattered light detector 34 is so constructed that it sends an intensity of the scattered light to the foreign matter determining device 35.

In the present embodiment, a vertical spot illumination device 40 is provided directly above the stage device 11. The vertical spot illumination device 40 comprises a white light source 41 for irradiating a light for a bright field illumination upon the wafer 1, a half mirror 43 for reflecting the white light 41 in vertical direction, and a lens 44 for forming the white light 41 into a spot shape, thereby illuminating the wafer 1, as the object to be inspected which is held on the stage device 11, in a spot light by irradiating the white light 41 vertically.

At the opposite position of the vertical spot illumination device 40 is provided an image pick-up device 45. Namely, the image pick-up device 45 is constructed with a line sensor, in which solid-state image sensor of photoelectric conversion type, such as CCD (charge Coupled Device) are aligned in a line, being positioned along with a Y direction orthogonal to a direction of movement of the stage, on an optical axis of the spot illumination device 40 at a penetrating side of the half mirror 43. Namely, the image pick-up device 45 is so constructed that it picks up an image of irregular reflection light under a bright field illumination.

To an image processing portion 46 of the image pick-up device 45 is connected a comparing portion 47, an output terminal of which is connected to a verifying portion 48. To an another input terminal of the comparing portion 47 and an another input terminal of the verifying portion 48 are connected the foreign matter determining device 35, and the foreign matter determining device 35 is so constructed that it sends the result of decision to a host computer 36 controlling the inspection device 10, the comparing portion 47 and the verifying portion 48.

Next, a method for inspecting foreign matters with the apparatus for inspecting foreign matters mentioned above, as the one embodiment of the present invention, will be explained by referring to FIG. 2.

When the laser beam 21 is irradiated from the inspection light illumination device 20 upon the wafer 1, at a low inclined angle as the inspection light, the scattered light 31 is generated from the foreign matter 5 and the circuit pattern (not shown in the figure) which are adhered and formed upon the first main surface 2 of the wafer 1 under the dark field illumination with the irradiation of the laser beam 21. This scattered light is collected by the objective lens 32, and an image of this is formed upon the scattered light detector 34 through the relay lens 33.

At this moment, since it has a regularity, the scattered light 31 from the circuit pattern is shielded by a space filter which is provided at the Fourier transformation plane of the pattern surface of the wafer 1 or a light shielding element of such as a photo detector (not shown in the figure). On the other hand, since the scattered light 31 from the foreign matter 5 is irregular, it forms an image upon the scattered light detector 34, passing through the space filter or the photo detector. Therefore, only the foreign matter can be detected.

And, the detection signal, which is detected by the scattered light detector 34 upon the scattered light 31 from the foreign matter 5 under the dark field illumination, is inputted into the foreign matter determining device 35. The foreign matter determining device 35 determined whether the foreign matter 5 present or not, on the basis of this detected signal, and also determines the coordinate position of the foreign matter 5 by referring to the data for decision as well as the data of the coordinate position from the controller 14 of the stage device 11. The coordinate position which is identified in this manner is outputted from the foreign matter determining device 35, for example, to the host computer 36 for totally executing the inspection apparatus 10, as well as to the comparing portion 47 and the verifying portion 48 which are electrically connected to the image pick-up device 45.

When the coordinate position of the foreign matter 5 sent from the foreign matter determining device 35 comes into an image pick-up position of the image pick-up device 45, i.e., within a spot from the vertical spot light illumination device 40, the comparing portion 47 takes in the image signal under the bright field illumination from the image pick-up-device 45. According to the function of the foreign matter determining device 35, since there must be adhered the foreign matter 5 at that coordinate position, the foreign matter 5 should comes out in that image as shown in FIG. 3(a). Namely, an image of the object to be inspected is obtained herewith.

After that, when the coordinate position which is shifted by a distance of one chip portion 4 from that of the foreign matter 5 sent from the foreign matter determining device 35, i.e., the coordinate position corresponding to that of the foreign matter 5 in an another chip portion 4 adjoining to that on which the foreign matter 5 is adhered, comes into the image pick-up position of the image pick-up device 45, the comparing portion 47 takes in the image signal under the bright field illumination from the image pick-up device 45. According to the function of the foreign matter determining device 35, since there is not adhered the foreign matter 5 at that coordinate position, the foreign matter 5 should not comes out in that image as shown in FIG. 3(b).

Following to that, as shown in FIGS. 3(a) through (d), the comparing portion 47 compares the coordinate position of the chip portion 4 on which the foreign matter 5 must be adhered, i.e., the image obtained at the coordinate position of the object to be inspected (in FIG. 3(a)), with the coordinate position of the chip portion on which the foreign matter 5 is not be adhered, i.e., the reference image at the coordinate position to be compared (FIG. 3 (b)). Namely, as shown in FIG. 3(d), the comparing portion 47 is in such condition that it takes in a pair of images of the same parts of a pair of the chip portions 4 and 4 which are adjacent with each other so as to compare them. And, a difference image shown in FIG. 3(c) is formed from the image of the object on which the foreign matter 5 is adhered as shown in FIG. 3(a) and the reference image shown in FIG. 3(b). The difference between the image in FIG. 3(a) and the image in FIG. 3(b) should be only the foreign matter 5, therefore, only a foreign matter image 6 is extracted as shown in FIG. 3(c).

And, the comparing portion 47 sends the foreign matter image 6 extracted to the verifying portion 48. The verifying portion 48 verifies that the decision on presence of foreign matter which is made by the foreign matter determining portion 35 is correct, when the foreign matter image 6 is sent from the comparing portion 47, relating to the coordinate position of the foreign matter 5 which is sent from the foreign matter determining portion 35. On the contrary to this, when the foreign matter image 6 relating to the coordinate position of the foreign matter 5 sent from the foreign matter determining portion 35 is not sent from the comparing portion 47, then the verifying portion 48 verifies that the decision on presence of foreign matter which is made by the foreign matter determining portion 35 is in error. And, when verifying the error, the verifying portion 48 send that effect to the host computer 36. Further, a reference numeral 100 is a monitor display for displaying various information related to the foreign matter, which are processed by the host computer 36 mentioned above.

Figure 4A:
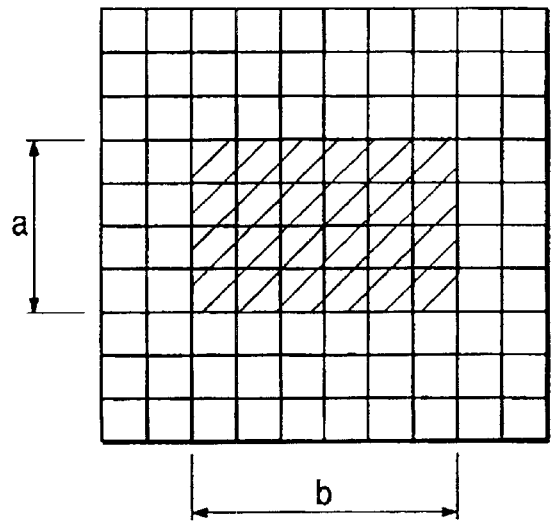
FIGS. 4(*a*) through (*d*) show explanatory view of classifying function, in particular, (a) a function of identifying vertical and horizontal sizes of the foreign matter, (b) a function of identifying other sizes of the foreign matter, (c) a function of identifying a circular foreign matter, and (d) a function of identifying a thin and long foreign matter.
Figure 4B:
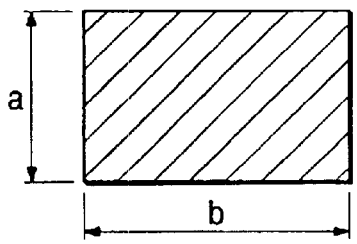
Figure 4C:
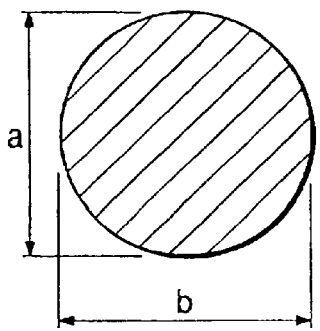
Figure 4D:
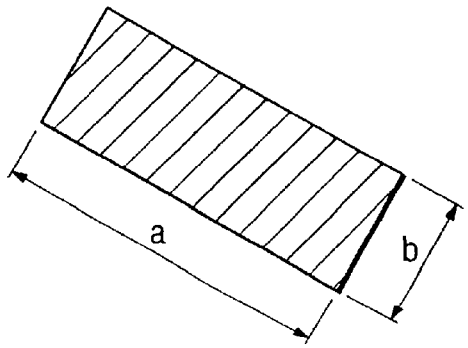

Further, the extracted foreign matter image 6 is transferred to the classifying portion 49. The classifying portion 49 classifies the foreign matter 5 in the sizes, shape, color and property thereof, such as whether it is organic or inorganic matter, according to an algorithm which is set previously. For example, as is shown in FIG. 4(a), the sizes of the foreign matter image 6 can be determined in the vertical and horizontal directions, by counting pixels of the foreign matter image 6. And, an area of the foreign matter 5, i.e., the size thereof can be determined by the product (a×b) between the vertical length a and the horizontal length b of the foreign matter image 6, as shown in FIG. 4(b). By the quotient (a/b) between the vertical length a and the horizontal length b of the foreign matter image 6, the shape of the foreign matter 5 is determined. For instance, in case where a/b=1, the foreign matter 5 is determined to be circular in the shape thereof, as shown in FIG. 4(c). And, in case where a/b>1 or a/b<1, the foreign matter 5 is determined to be in thin and long in the shape, as shown in FIG. 4(d).

Since the white light source 41 is used for the vertical spot light illumination, it is possible to determine the color of the foreign matter image 6, on the basis of the hue and the brightness thereof (i.e., gradation which forms the image). As a result of this, for example, if an entire of the foreign matter extracted has the hue and the degradation which are almost similar to those of a deep blue group, then the foreign matter can be assumed to be a layer of dielectric being in flat in the shape and almost uniform in the thickness.

Further, it is also possible to acknowledge the existence of a concave-convex upon the surface with use of the scattered light signal of the foreign matter which is detected by the scattered light detector, as well as the sizes and the property of the foreign matter which is determined by the foreign matter image 6. Namely, when the laser beam 21 as the inspection light is irradiated upon the wafer 1 at the low inclined angle by the inspection light illumination device 20, therewith the scattered light 31 is generated from the foreign matter 5 under the dark field illumination. Since the intensity of the scattered light is changed in relation with an area of the cross section and the concave-convex upon the surface, the condition of concave-convex upon the surface can be acknowledged by analyzing by use of the intensity of the scattered light recorded at the detection thereof and the length of the foreign matter in the direction normal to that of the laser irradiation which is calculated from the foreign matter image. As a result of this, for example, in case where the concave-convex is small, the foreign matter is determined as the inorganic matter, such as silica (glass) or silicon chip and metal chips, etc. If the concave-convex is large, it is determined as the organic matter, such as dust caused from or by human being and/or resin, etc.

The result of the classification, which is classified in the manner mentioned in the above, is sent from the classifying portion 49 to the host computer 36. The host computer 36 produces the various data shown in FIGS. 5(a) through (d), appropriately, by using the classification data from the classifying portion 49, and the data of coordinate positions and the number of the foreign matters 5 from the foreign matter determining portion 35, so as to output it appropriately through an output device, such as a monitor or a printer or the like. An operator, therefore, is able to manage production processes of IC exactly and quickly.

FIG. 5(a) shows maps for respective sizes of the foreign matters, which is produced by the size data of the foreign matter and the coordinate position data thereof. FIG. 5(b) is a histogram for respective sizes of the foreign matters, in which the size of the foreign matter is allotted to the horizontal axis as a variable divided into sections, while the number of detection is allocated to the vertical axis as the number of the measured values belonging to the respective sizes of the foreign matters.

FIG. 5(c) shows maps for respective shapes of the foreign matters, which is produced by the shape data of the foreign matter and the coordinate position data thereof. FIG. 5(d) is a histogram for respective shapes of the foreign matters, in which the shape of the foreign matter is allotted to the horizontal axis as a variable divided into sections, while the number of detection is allocated to the vertical axis as the number of the measured values belonging to the respective shapes of the foreign matters.

FIG. 5(e) is a graph for showing a result of analysis in a time sequence, which is produced by the date of inspection, the foreign matter size data, the foreign matter shape data (for example, thin and long) and the property data, such as the data of organic matter. However, in place of the time sequence, a lot number or a wafer number can be used therefor.

According to the one embodiment mentioned in the above, following effects can be obtained therewith.

(1) By determining the sizes, shape, color and the property of the foreign matter in addition to the coordinate position thereof with the inspection apparatus, the operator is able to manage the production processes of IC exactly and quickly, thereby increasing yield rate of the production of IC.

(2) The decision, which is made in the detecting portion upon the detection of the scattered light detector, is verified through the verifying portion which is connected to the image picking-up device operating under the bright field illumination, therefore it is possible to increase up the accuracy in inspection with the detecting apparatus, thereby increasing quality and reliability thereof, together with (1) mentioned in the above.

(3) Since the sizes, shape, color and the property of the foreign matter other than the coordinate position thereof, without using an inspection apparatus of exterior of foreign matter which takes a long time for testing, or a foreign matter analyzing apparatus which is extremely expensive, therefore, it is possible to reduce the time for inspection and for reviewing for an unit of area (i.e., for an each piece of wafer), very much. As a result of this, not only the inspection on all number of the lots, but also the management of the IC production process by the operator can be realized with accuracy and rapidity.

Figure 6:
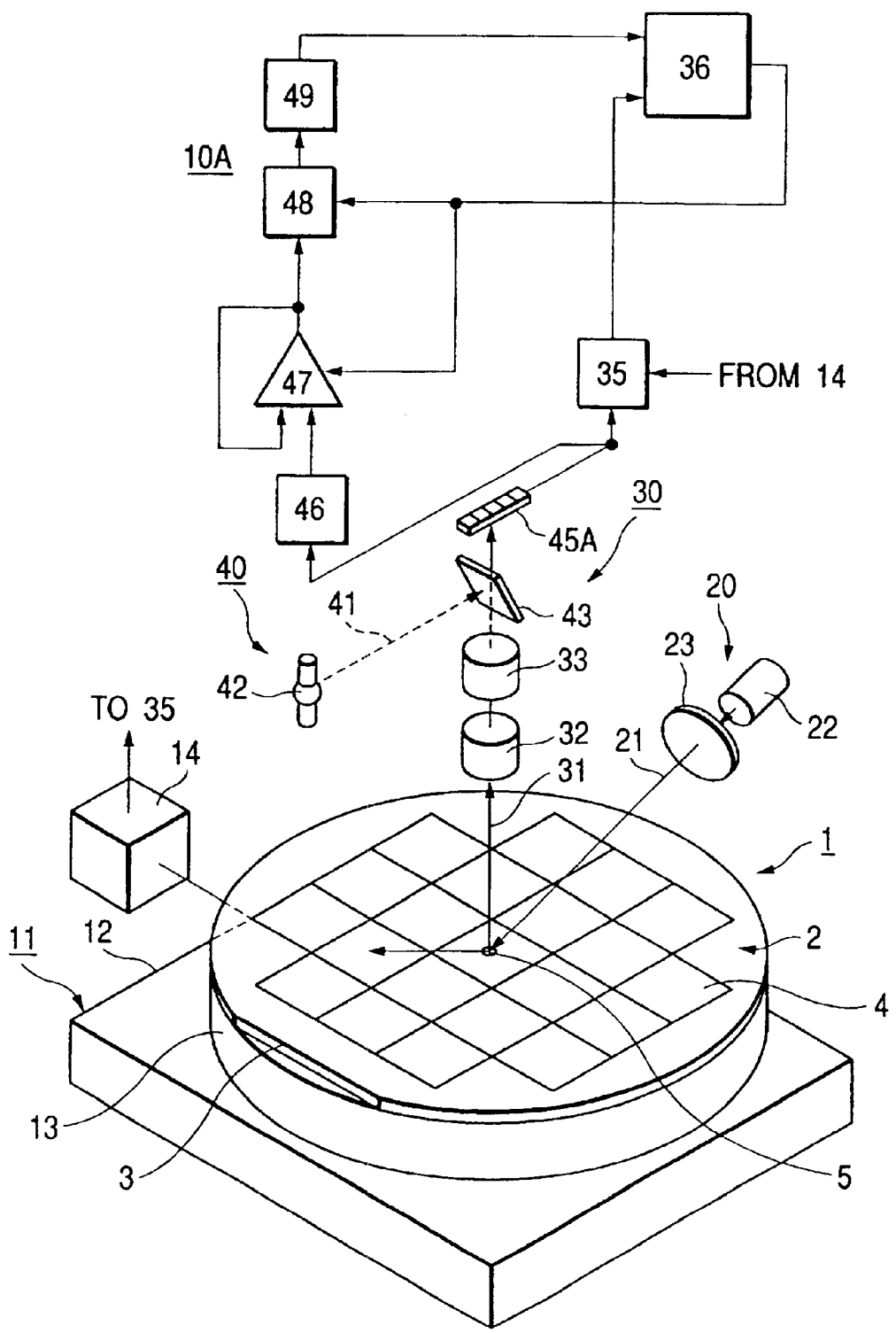
FIG. 6 shows a perspective view of a first variation of the apparatus for detecting foreign matter, in accordance with the present invention mentioned in the above.
Figure 7:
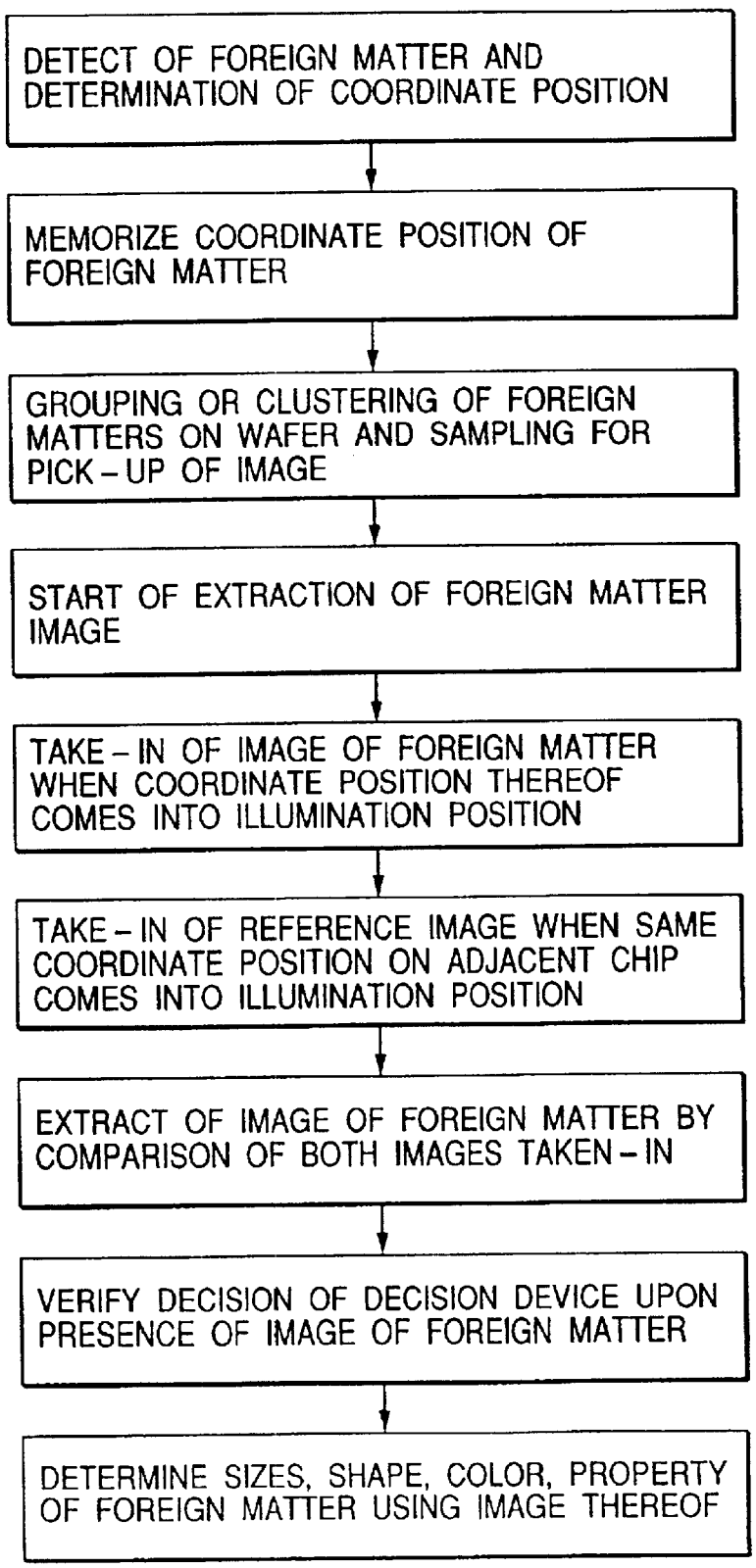
FIG. 7 shows a flow of a method for detecting foreign matter being processed with use of the foreign matter detecting apparatus, in accordance with the first variation mentioned in the above.

FIG. 6 shows a perspective view of a first variation of the apparatus for detecting foreign matter in accordance with the present invention mentioned in the above. FIG. 7 shows a flow of a method for inspecting foreign matter, processed with use of the inspection apparatus in accordance with the first variation mentioned in the above, and FIGS. 8(a) and (b) shows functions thereof.

The aspects of the inspection apparatus 10A according to the present first variation, being different from the inspection apparatus 10 mentioned in the above, lie in that the vertical spot illumination device 40 is used in common with the inspection light illumination device 20 in the optical system thereof, and that the image pick-up device 45A is so constructed that it is used in common with the scattered light detector.

In the inspection method with use of the inspection apparatus 10A according to the first variation, as shown in FIG. 7, first, the coordinate position of the foreign matter S upon the first main surface 2 of the wafer 1 is determined, all over the surface thereof, with the scattered light detector-and-image picking-up device 45A and the foreign matter determining device 35. Those coordinate positions are memorized into a memory (not shown in figure) in the host computer 36.

Figure 8A:
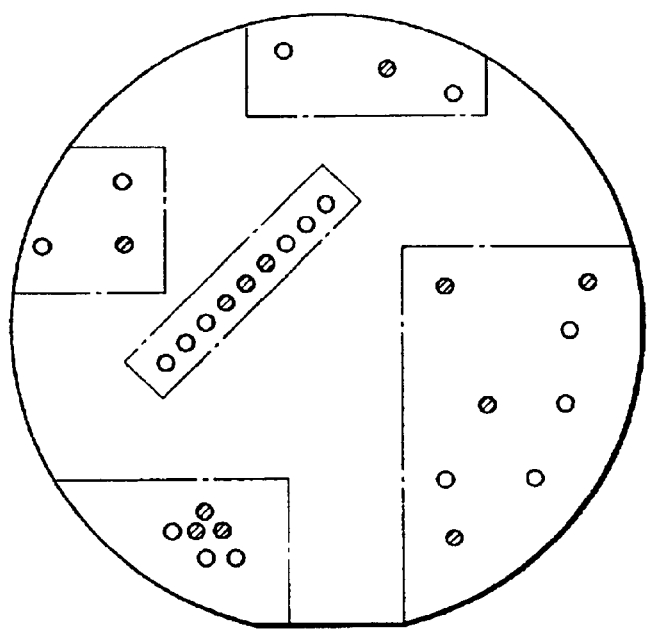
FIGS. 8(*a*) and (*b*) show functions of the foreign matter detecting apparatus, in accordance with the first variation mentioned in the above, in particular, (a) shows a function of grouping and (b) of clustering.

For example, the host computer 36 executes grouping (bringing the foreign matters near in the distance together)

on a group of the foreign matters 5 all over the first main surface 2 of the wafer 1, as shown in FIG. 8(a), and carries out sampling on representative one of each group as a target to be picked up with the image thereof. Since, with this, the targets to be taken the images can be reduced in the number thereof, therefore the time for the inspection can be further shorten.

Figure 8B:
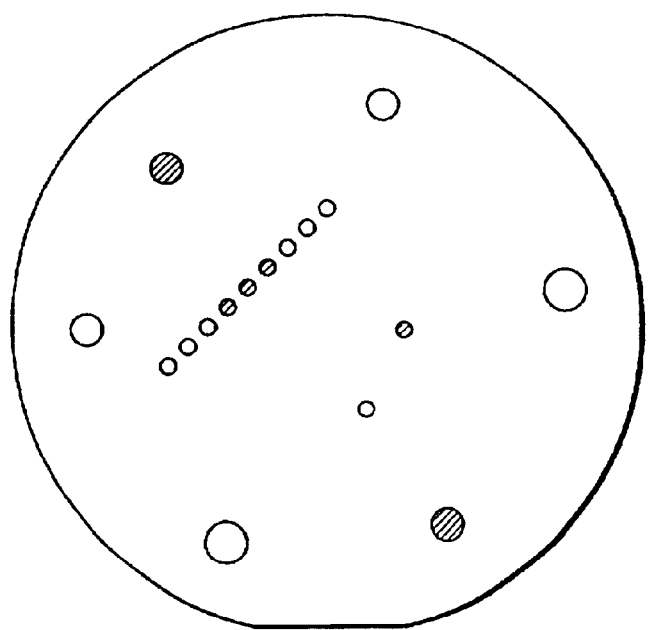

Further, the host computer 36 carries out clustering (classifying the sizes of the foreign matters by the intensity of scattered light) on the group of the foreign matters 5 all over the first main surface 2 of the wafer 1, as shown in FIG. 8(b), and carries out sampling on representative one of each class as an object to be picked up with an image thereof. Since, with this, the targets to be taken the images can be reduced in the number thereof, therefore the time for the inspection can be further shorten. By the way, the host computer 36 designates a sequential order of the picking-up of images in such that it can be done with the distance at the shortest, thereby further shortening the time for inspection, and increasing efficiency in the inspection.

Those coordinate positions of the targets, which are designated in the manner mentioned in the above, are sent from the host computer 36 to the verifying portion 48. When the coordinate position of the designated foreign matter 5 comes into the image pick-up position of the scattered light detector-and-image picking-up device 45A, i.e., within a spot from the vertical spot light illumination device 40, the comparing portion 47 takes in the image signal under the bright field illumination from the scattered light detector-and-image picking-up device 45A.

After that, the comparing portion 47 takes in the image signal at the same coordinate position on the adjacent chip portion 4. Next, the comparing portion 47 compares the image at the coordinate position where there should be adhered the foreign matter 5 to the image of the chip portion 4 taken in afterward, where no foreign matter 5 is adhered, so as to extract the foreign matter image 6.

Then, the comparing portion 47 sends the extracted foreign matter image 6 to the verifying portion 48. The verifying portion 48 verifies that the decision of presence of foreign matter which is made by the foreign matter deciding portion 35 is correct, when the foreign matter image 6 is sent from the comparing portion 47, relating to the coordinate position of the foreign matter 5 which is designated by the host computer 36. On the contrary to this, when the foreign matter image 6 relating to the coordinate position of the foreign matter 5 designated by the post computer 36 is not sent from the comparing portion 47, then the verifying portion 48 verifies that the decision of presence of foreign matter which is made by the foreign matter deciding portion 35 is in error. And, when verifying the error, the verifying portion 48 send that effect to the host computer 36.

Further, the extracted foreign matter image 6 is transferred to the classifying portion 49. The classifying portion 49 classifies the foreign matter 5 in the sizes, shape, color and property thereof, such as whether it is organic or inorganic matter, according to an algorithm which is set previously. The result of classification of the classified foreign matters 5 is sent from the classifying portion 49 to the host computer 36. The host computer 36 produces the various data appropriately, by using the classification data from the classifying portion 49, the data of coordinate position and the number of the foreign matters 5 from the foreign matter determining portion 35, as well as the intensity of the scattered light, so as to output it appropriately through an output device, such as a monitor or a printer or the like.

Figure 9:
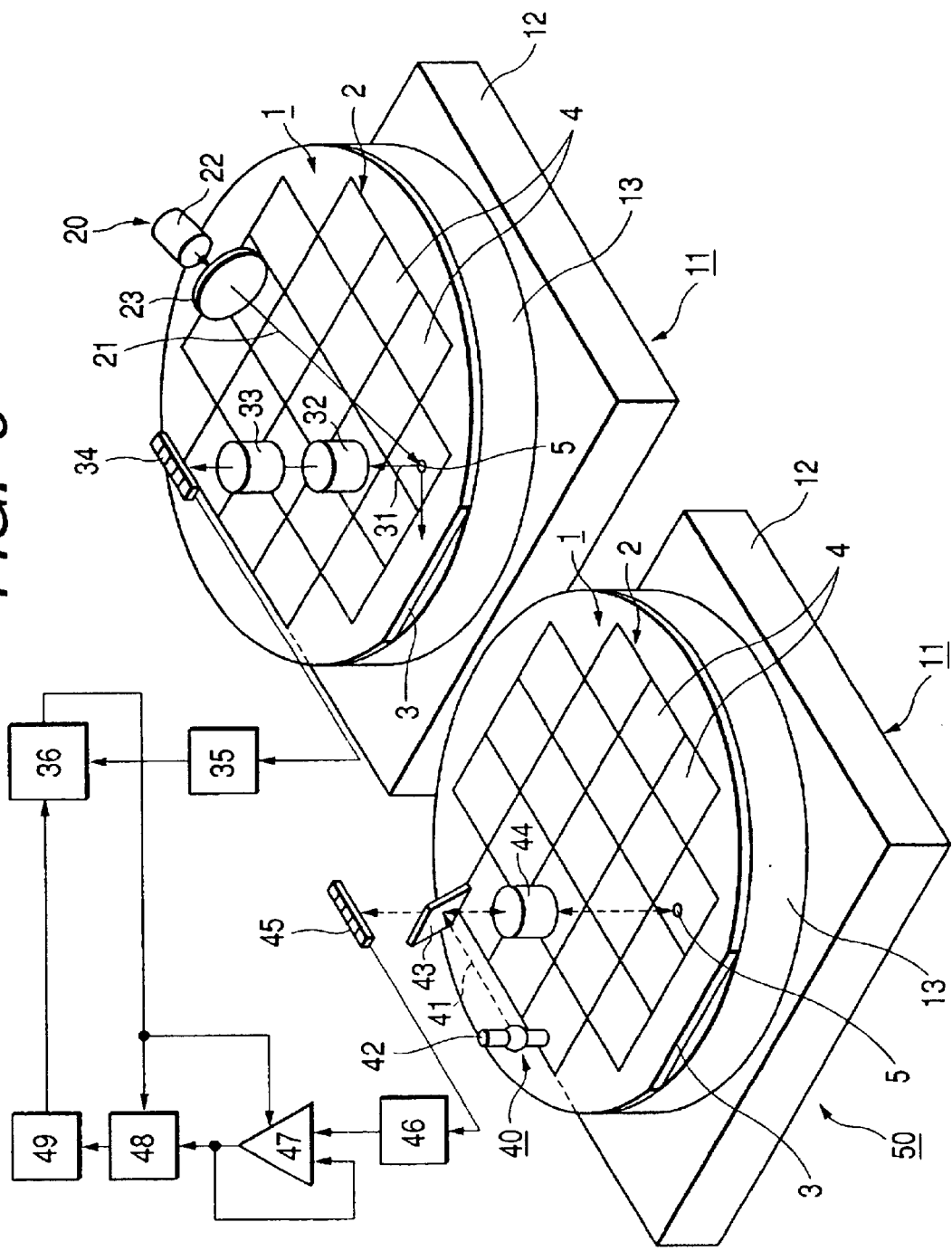
FIG. 9 shows a perspective view of a second variation of the apparatus for detecting foreign matter, in accordance with the present invention mentioned in the above.

FIG. 9 is a perspective view of a second variation of the apparatus for detecting foreign matter in accordance with the present invention mentioned in the above.

An aspect of the inspection apparatus 10B according to the present second variation, being different from the inspection apparatus 10 mentioned in the above, lies in that an image pick-up stage 50 for picking-up the image under bright field illumination is exclusively provided, which comprises the vertical spot light illumination device 40, the image pick-up device 45, etc.

Since the method for inspecting foreign matter in the inspection apparatus 10B follows that of the inspection method carried out in the first variation mentioned in the above, the explanation thereof in detail is omitted herewith. However, the image pick-up stage 50 under the bright field illumination is provided in the present inspecting apparatus 10B for foreign matter according to the second variation, therefore, the detection of foreign matter, the determination of the coordinate position and the extraction of the foreign matter image can be processed in parallel, thereby shortening the time for inspection as a whole.

Figure 10:
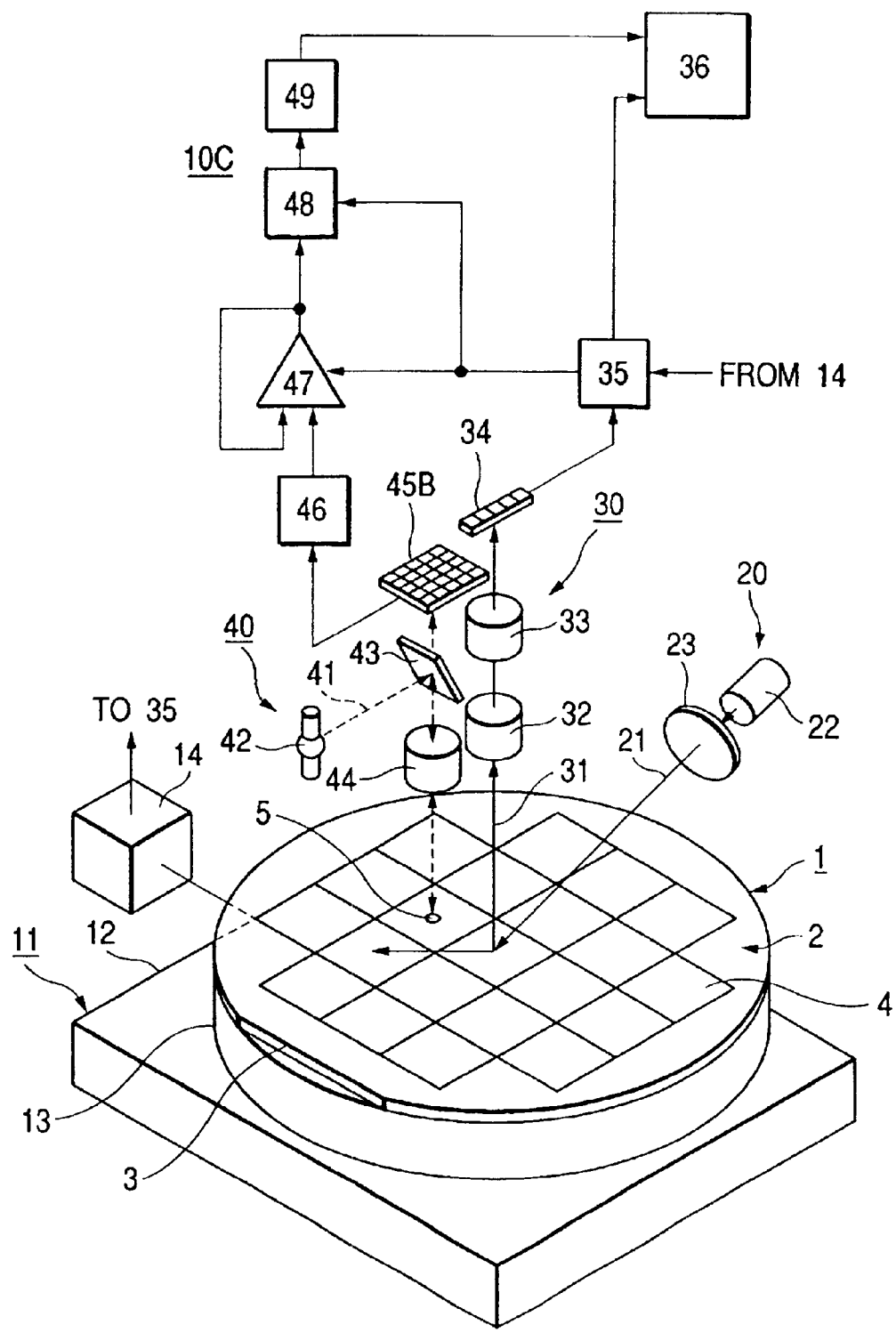
FIG. 10 shows a perspective view of a third variation of the apparatus for detecting foreign matter, in accordance with the present invention mentioned in the above.

FIG. 10 is a perspective view of a third variation of the apparatus for inspecting in accordance with the present invention mentioned in the above.

An aspect of the inspection apparatus 10C according to the present second variation, being different from the inspection apparatus 10 mentioned in the above, lies in that the image pick-up device 45 is changed form the line sensor into an area sensor 45B.

The method for inspection with the inspection apparatus 10C also follows that of the inspection method carried out in the first variation mentioned in the above, and it carries out the inspection according to the flow chart of FIG. 7, therefore, the explanation thereof in detail is omitted herewith.

With this inspection apparatus 10C according to the third embodiment, in which there is provided the image pick-up device of the area sensor, therefore it is possible to pick-up the foreign matter image under a standstill condition of the stage so as to obtain a high resolution power with ease, thereby increasing the reliability as well as the quality in the result of the inspection of foreign matter.

In the above, although the invention made by inventors of the present inventions was explained in detail on the basis of the above embodiment and the variations thereof, however, it should not be restricted only to the embodiment and the variations thereof, and it is needless to say that it can be modified within a breadth without deviating beyond the gist of the invention.

For instance, the determination in the foreign matter position under the bright field illumination should not be restricted only with the construction in which it is carried out by the optical shutter element, but it also can be carried out by such a construction that comparison of the data detected at the same position on the repeated patterns is done. In the case, the data to be compared with can be the detected data of the adjacent chip, a predetermined pattern which is memorized previously, or a standard pattern.

As the image pick-up device can be used not only that which uses the line sensor, but also that which uses the area sensor or an image pick-up tube, or the like.

In the above, there is mainly explained the invention which is made by the inventors, in particular, in a case where it is applied to a field of the foreign matter or defect inspection technology for wafers, as the background of the present invention, however, it should not be limited only to this, and can be applied to the whole of the foreign matter or defect detecting technology for a plate-like object, in general, including a photo mask or a liquid crystal panel, etc.

Effects which can be obtained with the embodiment and the variations thereof will be explained briefly as follows:

By determining the sizes, shape, color and the property of the defect or foreign matter in addition to the coordinate position thereof with the inspection apparatus, the operator is able to manage the production processes of IC exactly and quickly, thereby increasing yield rate of the production of IC.

The decision, which is made in the foreign matter detecting portion upon the detection of the scattered light detector, is verified through the verifying portion which is connected to the image picking-up device operating under the bright field illumination, therefore it is possible to increase up the accuracy in inspection with the inspection apparatus, thereby increasing quality and reliability of thereof, together with the effect mentioned in the above.

Since the sizes, shape, color and the property of the foreign matter other than the coordinate position thereof, without using a inspection apparatus of exterior of foreign matter which takes a long time for testing or a defect analyzing apparatus which is extremely expensive, therefore it is possible to reduce the time for inspection and for reviewing for an unit of area (i.e., for an each piece of wafer), very much. As a result of this, not only the inspection on all number of the lots, but also the management of the IC production process by the operator can be realized with accuracy and rapidity.

Next, an explanation on an another embodiment according to the present invention will be given in detail by referring to the attached drawings. In this another embodiment, the inspection apparatus 10 is same to that shown in FIG. 1 in the construction thereof, therefore the explanation of it will be omitted here.

Figure 11:
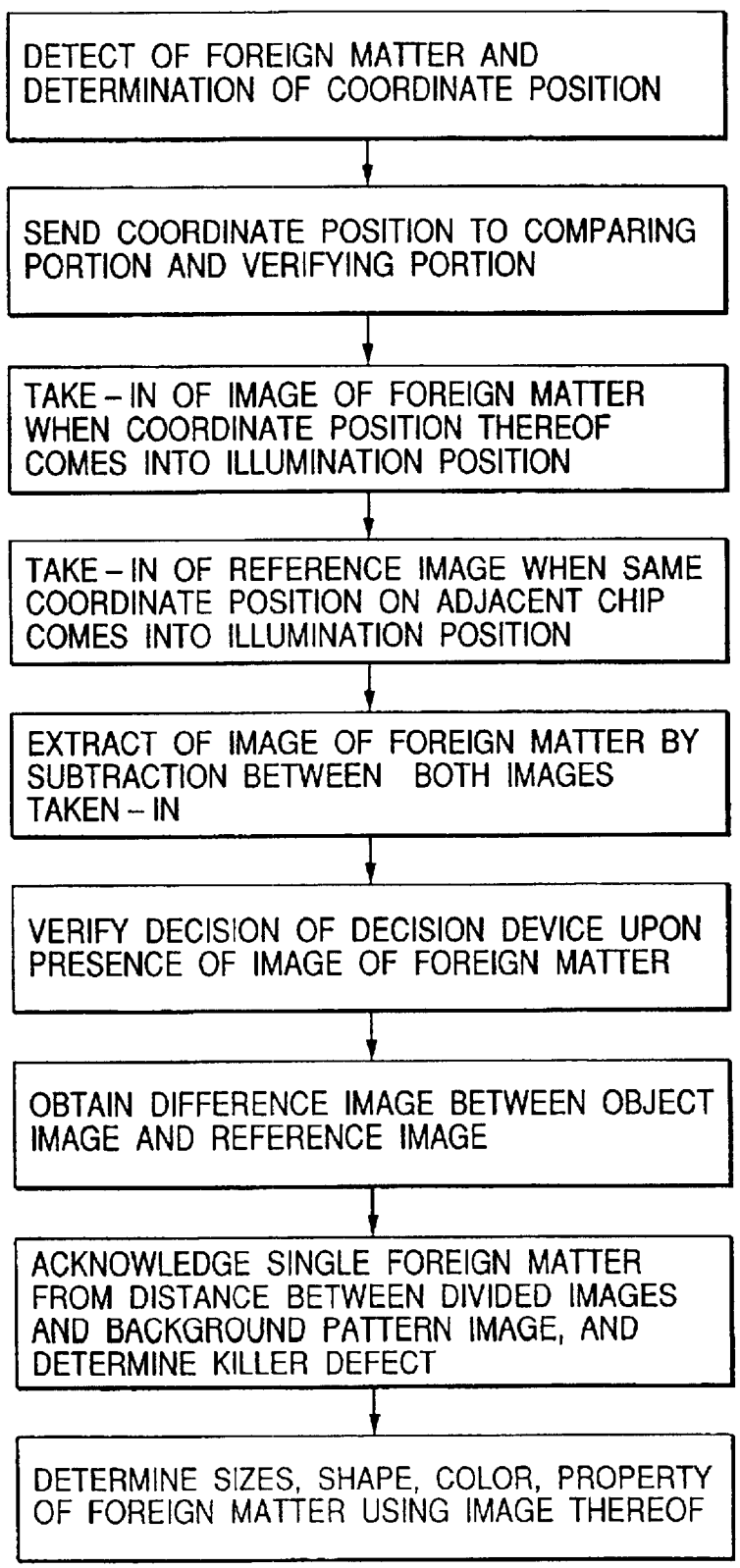
FIG. 11 shows a flow of a method for detecting foreign matter being processed in an apparatus for detecting foreign matter, in accordance with another embodiment of the present invention.
Figure 12D:
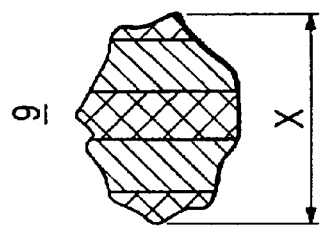
FIGS. 12(a) through (d) show views for explaining an acknowledgment of a single foreign matter when the image is divided into three (3) in the foreign matter detecting method, according to the another embodiment of the present invention mentioned in the above.
Figure 12C:
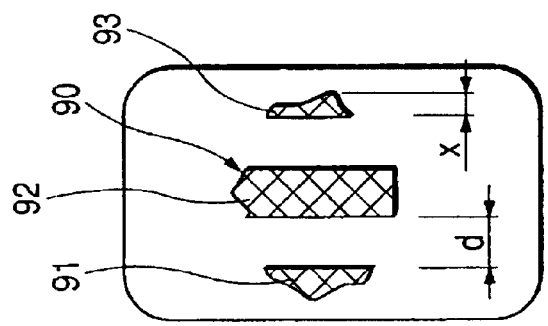
Figure 12B:
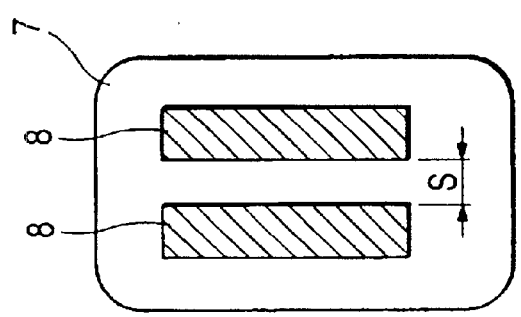
Figure 12A:
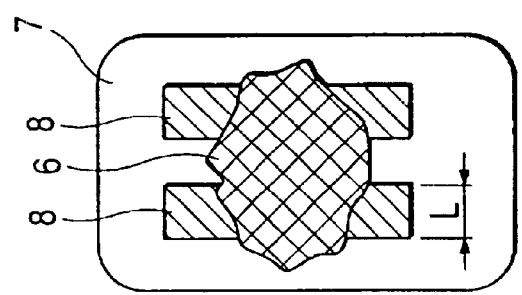

And, the method for inspection according to the another embodiment of the present invention, which is carried out with the inspection apparatus 10 of the construction mentioned in the above, will be explained by referring to attached FIG. 11.

First of all, in the same manner as shown in FIG. 2 mentioned above, when the laser beam 21 is irradiated from the inspection light illumination device 20 upon the wafer 1, at a low inclined angle as the inspection light, the scattered light 31 is generated from the foreign matter 5 and the circuit pattern (not shown in the figure) which are adhered and formed upon the first main surface 2 of the wafer 1 under the dark field illumination with the irradiation of the laser beam 21. This scattered light is collected by the objective lens 32, and an image of this is formed upon the scattered light detector 34 through the relay lens 33.

At this moment, since it has a regularity, the scattered light 31 from the circuit pattern is shielded by a space filter which is provided at the Fourier transformation plane of the pattern surface of the wafer 1 or a light shielding element of such as a photo detector (not shown in the figure). On the other hand, since the scattered light 31 from the foreign matter 5 is irregular, it forms an image upon the scattered light detector 34, passing through the space filter or the photo detector. Therefore, only the foreign matter can be detected.

And, the detection signal, which is detected by the scattered light detector 34 upon the scattered light 31 from the foreign matter 5 under the dark field illumination, is inputted into the foreign matter determining device 35. The foreign matter determining device 35 determined whether the foreign matter 5 present or not, on the basis of this detected signal, and also determines the coordinate position of the foreign matter 5 by referring to the decision data as well as the data of the coordinate position from the controller 14 of the stage device 11. The coordinate position which is identified in this manner is outputted from the foreign matter determining device 35, for example, to the host computer 36 for totally executing the inspection apparatus 10, as well as to the comparing portion 47 and the verifying portion 48 which are electrically connected to the image pick-up device 45.

When the coordinate position of the foreign matter 5 sent from the foreign matter determining device 35 comes into an image pick-up position of the image pick-up device 45, i.e., within a spot from the vertical spot light illumination device 40, the comparing portion 47 takes in the image signal under the bright field illumination from the image pick-up device 45. According to the function of the foreign matter determining device 35, since there must be adhered the foreign matter 5 at that coordinate position, the foreign matter 5 should comes out in that image as shown in FIG. 3(a). Namely, an image of the object to be inspected is obtained herewith.

After that, when the coordinate position which is shifted by a distance of one chip portion 4 from that of the foreign matter 5 sent from the foreign matter determining device 35, i.e., the coordinate position corresponding to that of the foreign matter 5 in an another chip portion 4 adjoining to that on which the foreign matter 5 is adhered, comes into the image pick-up position of the image pick-up device 45, the comparing portion 47 takes in the image signal under the bright field illumination from the image pick-up device 45. According to the function of the foreign matter determining device 35, since there is not adhered the foreign matter 5 at that coordinate position, the foreign matter 5 should not comes out in that image as shown in FIG. 3(b). Namely, a reference image of the object to be inspected is obtained herewith.

Following to that, as shown in FIGS. 3(a) through (d), the comparing portion 47 subtract from the coordinate position of the chip portion 4 on which the foreign matter 5 must be adhered, i.e., the image obtained at the coordinate position of the object to be inspected (in FIG. 3(a)), the coordinate position of the chip portion on which the foreign matter 5 is not be adhered, i.e., the reference image at the coordinate position to be compared (FIG. 3(b)). Namely, as shown in FIG. 3(d), the comparing portion 47 is in such condition that it takes in a pair of images of the same parts of a pair of the chip portions 4 and 4 which are adjacent with each other so as to make an arithmetic process, i.e., subtraction of them. With this subtraction, a difference image shown in FIG. 3(c) is formed from the image of the object on which the foreign matter 5 is adhered as shown in FIG. 3(a) and the reference image shown in FIG. 3(b). The difference between the image in FIG. 3(a) and the image in FIG. 3(b) should be only the foreign matter 5, therefore, only a foreign matter image 6 is extracted on the difference image shown in FIG. 3(c).

And, the comparing portion 47 sends the foreign matter image 6 extracted to the verifying portion 48. The verifying portion 48 verifies that the decision on presence of foreign matter which is made by the foreign matter determining portion 35 is correct, when the foreign matter image 6 is sent from the comparing portion 47, relating to the coordinate position of the foreign matter 5 which is sent from the foreign matter determining portion 35. On the contrary to this, when the foreign matter image 6 relating to the coordinate position of the foreign matter 5 sent from the foreign matter determining portion 35 is not sent from the comparing portion 47, then the verifying portion 48 verifies that the decision on presence of foreign matter which is made by the foreign matter determining portion 35 is in error. And, when verifying the error, the verifying portion 48 send that effect to the host computer 36.

Further, the extracted foreign matter image 6 is transferred to the classifying portion 49. The classifying portion 49 classifies the foreign matter 5 in the sizes, shape, color and property thereof, such as whether it is organic or inorganic matter, according to an algorithm which is set previously. For example, as is shown in FIG. 4(*a*), the sizes of the foreign matter image 6 can be determined in the vertical and horizontal directions, by counting pixels of the foreign matter image 6. And, an area of the foreign matter 5, i.e., the size thereof can be determined by the product (a×b) between the vertical length a and the horizontal length b of the foreign matter image 6, as shown in FIG. 4(*b*). By the quotient (a/b) between the vertical length a and the horizontal length b of the foreign matter image 6, the shape of the foreign matter 5 is determined. For instance, in case where a/b=1, the foreign matter 5 is determined to be circular in the shape thereof, as shown in FIG. 4(*c*). And, in case where a/b>1 or a/b<1, the foreign matter 5 is determined to be in thin and long in the shape, as shown in FIG. 4(*d*).

Since the white light source 41 is used for the vertical spot light illumination, it is possible to determine the color of the foreign matter image 6, on the basis of the hue and the brightness (i.e., gradation which forms the image) thereof. As a result of this, for example, if an entire of the foreign matter extracted has the hue and the degradation which are almost similar to those of a deep blue group, then the foreign matter can be assumed to be a layer of dielectric being flat in the shape and almost uniform in the thickness.

Further, it is also possible to acknowledge the existence of a concave-convex upon the surface with use of the scattered light signal of the foreign matter which is detected by the scattered light detector, as well as the sizes and the property of the foreign matter which is determined by the foreign matter image 6. Namely, when the laser beam 21 as the-inspection light is irradiated upon the wafer 1 at the low inclined angle by the inspection light illumination device 20, therewith the scattered light 31 is generated from the foreign matter 5 under the dark field illumination. Since the intensity of the scattered light is changed in relation with an area of the cross section and the concave-convex upon the surface, the condition of concave-convex upon the surface can be acknowledged by analyzing by use of the intensity of the scattered light recorded at the detection thereof and the length of the foreign matter in the direction normal to that of the laser irradiation which is calculated from the foreign matter image. As a result of this, for example, in case where the concave-convex is small, the foreign matter is determined as the inorganic matter, such as silica (glass) or silicon chip and metal chips, etc. If the concave-convex is large, it is determined as the organic matter, such as dust caused by or from human being and/or resin, etc.

The result of the classification, which is classified in the manner mentioned in the above, is sent from the classifying portion 49 to the host computer 36. The host computer 36 produces the various data shown in FIGS. 5(*a*) through (*d*), appropriately, by using the classification data from the classifying portion 49, and the data of coordinate positions and the number of the foreign matters 5 from the foreign matter determining portion 35, so as to output it appropriately through an output device, such as a monitor or a printer or the like. An operator, therefore, is able to manage production processes of IC exactly and quickly.

By the way, it is found by the inventors of the present invention that such a phenomenon occurs that the foreign matter image comes to be divided in the inspection apparatus, as shown in FIG. 12(*c*), in a case where the foreign matter adheres bridging over the adjacent wiring patterns, and if the reference image of the object to be inspected at the coordinate position thereof is subtracted from the image of the object to be inspected at the coordinate position thereof. The reason of occurring such phenomenon could be considered as follows.

FIG. 12(*a*) shows the image of the object to be inspected at the coordinate position thereof, wherein a pair of wiring patterns 8 and 8 provided in parallel to each other appear on a background image 7, and the foreign matter 6 is in the condition it appers to bridge over the both wiring patterns 8 and 8. FIG. 12(*b*) shows the image of the reference object at the coordinate position thereof, wherein only the both wiring patterns 8 and 8 appear on the background image 7.

When the subtraction is made in the comparing portion 47, assuming that the value of the binary image signal of the background image 7 is white, the value of the foreign matter image 6 is equal to black, and the wiring pattern 8 to gray. Accordingly, subtracting FIG. 12(*b*) from FIG. 12(*a*), the difference image 9 comes into such the condition that the wiring pattern is remained in the color of pale gray within the foreign matter image 6. However, this difference image is processed into binary signal, the binary difference image 90 comes into a condition that it is divided into three (3) by the images 8 and 8 of the both wiring patterns, as shown in FIG. 12,(*c*).

In case that the foreign matter image 6 is acknowledged in the condition of being divided in this manner, there is a possibility for the classifying portion 49 to classify it into foreign matters in series and in small in the size. Namely, though the foreign matter 5 might cause a fetal or killer defect, such as wire break or short circuit, there is possibility that it is decided to be a minute defect or foreign matter which will not cause such the killer defect. For example, in a process of inspecting the foreign matter after the process of forming the wiring patterns, if the foreign matter of metal bridging over the wiring patterns is erroneously decided to be the minute foreign matter(s) located between them, it means that the foreign matter of the short circuit is overlooked, a step or measure for the killer defect is delayed to be taken. Therefore, the yield rate is decreased down. Accordingly, even in the case where the difference image 90 is acknowledged to be very fine or minute, there is a necessity to determine whether it is foreign matter image divided by the wiring pattern or the minute defect or foreign matter located between the wiring patterns.

With the present another embodiment, it is determined in the classifying portion 49 whether the difference image is the divided I-one or not, with following algorithm. First, a case will be explained where the difference image 90 is divided into three (3) or more by the adjoining wiring patter(s), as shown in FIG. 12(*c*), i.e., into a left-hand side image 91, a central image 92 and a right-hand side image.

As shown in FIG. 12(*c*), a distance d between the left-hand side image 91 and the central image 92, and a distance d between the central image 92 and the right-hand side image 93, a width L of the image of the wiring pattern 8 is calculated by subtraction therebetween. In a case where the difference by the subtraction comes to be a value equal or less than a preset value $\epsilon$, it is acknowledged to be the difference image 90 of a single foreign matter. And, as shown in FIG. 12(*d*), the width X in the direction orthogonal to the difference image 90 of the wiring pattern 8 is measured by means of a distance between the left edge of the left-hand side image 91 and the right edge of the right-hand side image 93. The foreign matter, which is decided to be the difference image 90 of the single foreign matter in this manner, is determined to be that which will cause the killer defect.

In a case where the difference by the subtraction comes to be in a value greater than a preset value $\epsilon$, the left-hand side image 91, the central image 92 and the right-hand side image 93 are determined to be minute defects, respectively, the width X of each of which is measured as the size of the respective defect. And, if the size of the left-hand side image 91, the central image 92 and the right-hand side image 93 is larger than S, i.e., the distance between the images 8 and 8 of the wiring patterns, it is decided to have a possibility of causing the killer defect, i.e., a possible defect, and if it is smaller than that, it is decided to be one which can not cause such the killer defect.

As shown in FIG. 13(*c*), the left-hand side image 94 and the right-hand side imager 95 are divided into two (2), the width L is obtained by subtraction of the distance d between the left-hand side image 94 and the right-hand side imager 95. In case where the difference value by the subtraction is smaller than the preset value $\epsilon$, it is determined to be the difference image of the single foreign matter. Namely, as shown in FIG. 13(*c*), the width X in the direction orthogonal to the difference image 90 of the wiring pattern 8 is measured by means of a distance between the left edge of the left-hand side image 94 and the right edge of the right-hand side image 95. And, this foreign matter is determined to be that which will cause the killer defect, i.e., the possible defect.

In a case where the difference by the subtraction comes to be in a value greater than a preset value $\epsilon$, the left-hand side image 94 and the right-hand side image 95 are determined to be minute defects or foreign matters, respectively, the width X of each of which is measured as the size of the respective one. And, if the size of the left-hand side image 94 and the right-hand side image 95 is larger than S, the distance between the images 8 and 8 of the wiring patterns, it is decided to have a possibility of causing the killer defect, i.e., the possible defect, and if it is smaller than that, it is decided to be one which can not cause such the killer defect.

Each information of all the foreign matters which are detected and determined in the manner mentioned in the above, and the result of the determination if it is the killer defect or the possible defect, they are arranged in a manner as shown in a Table 1 as below. Further, among those information relating to the foreign matter, the coordinates of chip and the coordinate position in chip are ones that can be obtained from the detection with the scattered light, and the information rather in detail, such as the defect sizes and whether it is killer defect or non-killer defect are ones that can be obtained on a basis of the image of the foreign matter under the bright field illumination. Those various information relating to the foreign matter are combined and displayed on a screen of the monitor display 100 mentioned above.

TABLE 1

| Defect No. | Coordinates of Chip | | Coordinate Position in Chip | | Defect Sizes | | | | | Killer Defect/ Non-Killer Defect |
|---|---|---|---|---|---|---|---|---|---|---|
| | Xc | Yc | X | Y | X | Y | U | V | Area | |
| 1 | 0 | 6 | 1998 | 812 | 1.51 | 1.55 | 1.29 | 0.46 | 1.8 | |
| 2 | 2 | 3 | 9234 | 1364 | 1.15 | 8.91 | 3.72 | 0.65 | 7.2 | |
| 3 | 2 | 8 | 6519 | 705 | 1.65 | 2.61 | 1.15 | 0.95 | 3.3 | Possible Defect |
| 4 | 2 | 10 | 7891 | 2910 | 0.49 | 2.3 | 1.94 | 0.14 | 0.8 | |
| 5 | 4 | 4 | 359 | 1007 | 1.47 | 2.22 | 1.1 | 0.76 | 2.5 | Killer Defect |
| 6 | 4 | 10 | 6519 | 2017 | 1.2 | 5.22 | 1.78 | 0.83 | 4.4 | Possible Defect |
| . | . | . | . | . | . | . | . | . | . | . |
| . | . | . | . | . | . | . | . | . | . | . |
| . | . | . | . | . | . | . | . | . | . | . |
| 22 | 12 | 6 | 214 | 4913 | 1.76 | 0.89 | 1.58 | 0.25 | 1.2 | |
| 23 | 13 | 8 | 1705 | 3279 | 0.84 | 2.2 | 1.53 | 0.29 | 1.3 | Killer Defect |

Further, the result of the inspection, such as the inspection information, the number of the foreign matters, the yield rate of the wafer for the respective processes, etc., are arranged in a manner as shown in a Table 2 as below.

TABLE 2

| Inspection Wafer Information | Product Name | 256 MDRAM | |
| --- | --- | --- | --- |
| | Lot ID | 123456 | |
| | Wafer ID | ABC | |
| | Chip Number | 157 | |
| | Chip Area (cm$^2$) | 1.56 | |
| | Inspection Process | Inspection After Completion of Wiring on 1$^{st}$ Layer | |
| | Inspection Time | 1998.02.24 10:18 | |
| Number of Foreign Matters/ Defects | Total Defect Number on Wafer | 23 | Ratio of Total Number of Defects |
| | Number of Killer Defects | 5 | 22% |
| | Number of Possible Defects | 8 | 35% |
| Yield Rate of Chips | Number of Chips with Detected Defect | 10 | Ratio to Total Chip Number |
| | Number of Chips with Killer Defect | 4 | 2.5% |
| | Number of Chips with Possible Defect | 6 | 3.8% |
| | Rate of Good Chip Product | | 93% |

TABLE 2-continued

| | | | |
|---|---|---|---|
| | Rate of Non-Good Chip Product | | 3% |
| Density of Defect | Density of Defect (Number/cm$^2$) | Max. Min. | 0.05 0.02 |
| | Defect Wafer Density (Number/cm$^2$) | Max. Min. | 0.05 0.02 |

Here, the rate of good chip product yi means a ratio of the number of chips which include neither the killer defect nor the possible defect therein, with respect to the total number of the chips, and the rate of non-good chip product fi means a ratio of the number of the chips in which are found the killer defects, with respect to the total number of chips. Further, the density of defect indicates the number of the foreign matters and the defects per an unit area. The density of defect follows a definition below and is displayed with two kinds, i.e., the maximum value and the minimum value of the range which is presumed. Namely, the density of defect Di is:

$$Di(\text{max.}) = -(1/A) \times \text{Ln}(yi)$$

$$Di(\text{min.}) = -(1/A) \times \text{Ln}(1-fi)$$

where A is the chip area, and Ln is the natural logarithm.

The defect wafer density wi is:

$Wi(\text{max.}) = $ (the number of the killer defects+number of possible defects)/(A×the number of chip products)

$Wi(\text{min.}) = $ (the number of the killer defects)/(A×the number of chip products)

Figure 14:
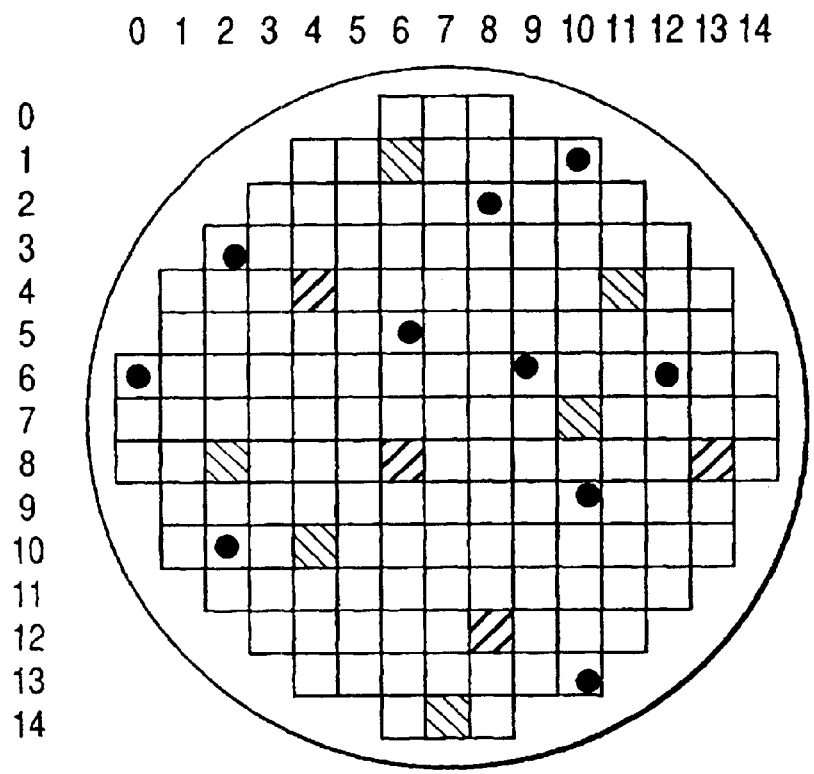
FIGS. 14 shows a map for a wafer on which are displayed fetal or foreign matters (killer defects) and/or bad chips in the foreign matter detecting method according to the another embodiment of the present invention mentioned in the above.

Further, as shown in FIG. 14, the killer defects and the non-good chips are displayed in a wafer map.

When the inspection is completed on a one lot, an information of the result of the inspection is displayed, as shown in Tables 3 and 4 below, for each of the lots, for instance on a screen of the display device (not shown in the figure) of the apparatus. Also, information of the result of the inspection is transferred to an external system of such as an analyzer system of the inspection information.

TABLE 3

| | |
|---|---|
| Product Name | 256 MDRAM |
| Lot ID | 123456 |
| Wafer ID | ABC |
| Chip Number | 157 |
| Chip Area (cm$^2$) | 1.56 |
| Inspection Process | Inspection After Completion of Wiring on 15$^{th}$ Layer |
| Inspection Time | 1998.02.24 10:18 |

TABLE 4

| Wafer ID | Information relating to Detected Defects | | | Information relating to Number of Chips | | | Yield Rate of Chips | | Defect Density (number/cm$^2$) | | | |
|---|---|---|---|---|---|---|---|---|---|---|---|---|
| | | | | | | | | | Di | | Wi | |
| | AA-1 | AA-2 | AA-3 | BB-1 | BB-2 | BB-3 | CC-1 | CC-2 | Max. | Min. | Max. | Min. |
| ABA | 18 | 4 | 5 | 9 | 4 | 5 | 0.94 | 0.03 | 0.04 | 0.02 | 0.08 | 0.02 |
| ABB | 26 | 8 | 15 | 22 | 8 | 14 | 0.86 | 0.05 | 0.10 | 0.03 | 0.07 | 0.03 |
| ABC | 23 | 5 | 8 | 10 | 4 | 6 | 0.94 | 0.03 | 0.04 | 0.02 | 0.05 | 0.02 |
| ABD | 17 | 3 | 8 | 11 | 3 | 8 | 0.93 | 0.02 | 0.05 | 0.01 | 0.07 | 0.01 |
| ABE | 22 | 6 | 13 | 15 | 6 | 9 | 0.90 | 0.04 | 0.06 | 0.02 | 0.10 | 0.02 |
| ABF | 24 | 6 | 18 | 24 | 6 | 18 | 0.85 | 0.04 | 0.11 | 0.02 | 0.02 | 0.02 |

In the above Table, the symbols are as follows:
AA-1: the total defect number on wafer;
AA-2: the number of killer defects;
AA-3: the number of possible defects;
BB-1: the number of chips with detected defect;
BB-2: the number of chips with killer defect;
BB-3: the number of chips with possible defect;
CC-1: the rate of good chip product; and
CC-1: the rate of non-good chip product.

Since the inspection apparatus of the scattered light detection type detects only the foreign matter(s) upon the most surface of the wafer, therefore, if the foreign matter lies on the pattern, it results into the defect of the product. By managing the the rates of the good and the non-good chip products, it is possible to prospect the yield rate at a final inspection of the products. Further, from the distribution of the non-good chip product, it is possible to determine whether the foreign matter is a random foreign matter or not. In a case where the foreign matter is the random foreign matter, assuming that the foreign matters takes the Poisson distribution, the following equation can be obtained, $$yi = \exp(-\times A \times Di)$$

where A is the area of the chip. Then, the density of the defect Di (here, suffix i indicates the process in number) in each of the processes can be calculated. Accordingly, a countermeasure will be taken for the foreign matters and/or defects in the process depending on a degree of deviation or separation from a value for managing the density of defect, which is distributed to each process. Those methods of managing the foreign matters and/or defects in the process on a way, differing from that of the conventional method in which the density of defect is calculated from the number of the foreign matters and/or defects and the area of inspection, work out the density of defects Di in a manner similar to a yield rate mode for final inspection, namely, which can represented by the equation below:

$$y = \exp(-A \times D)$$

where y is the rate of yield, A the area of the chip, and D the density of defects. Therefore, it is possible to extract or pick up the process which gives the effect directly onto the increase of the rate of yield in the final process.

Namely, according to the another embodiment of mentioned above, following effects can be achieved.

(1) Since the sizes of the foreign matter(s) is able to be outputted without using such the apparatus that takes long time for inspection and/or a plurality units thereof, therefore the time length for inspecting one (1) piece of the wafer can be shorten greatly, as a result of this, it is possible to contribute to an improvement of the yield rate in an early stage.

(2) By supplying the inspection data which directly relates to a reduction of the density of defects in the model of the yield rate in a probe inspection, it is possible to catch a point for increase of the yield rate, as well as to decide the propriety of the countermeasure therefor, in a short time.

(3) The decision, which is made in the detecting portion upon the detection of the scattered light detector, is verified through the verifying portion which is connected to the image pick-up device operating under the bright field illumination, therefore it is possible to increase up the accuracy in inspection with the detecting apparatus, thereby increasing quality and reliability of thereof, together with (1) mentioned in the above.

(4) By judging whether the divided portions be in a singled foreign matter or not so as to measure the diameter of particle(,s), it is possible to measure the sizes of the foreign matter(s) with accuracy more than even before.

(5) Since it is possible to decide the fatality of the foreign matter (i.e., killer defect or not) from the groundwork pattern and the sizes and/or the property of the foreign matter, the efficiency of the method of inspection can be risen up all the more.

(6) Since the rate of good chip product and the density of defects in a chip to be inspected can be calculated, the efficiency with use of the inspection method can be risen up all the more.

FIG. 15 is an view for explaining a function of acknowledgment of the single foreign matter in a first variation of the inspection method, according to the another embodiment of the present invention mentioned in the above.

Figures 15A, 15B, 15C:
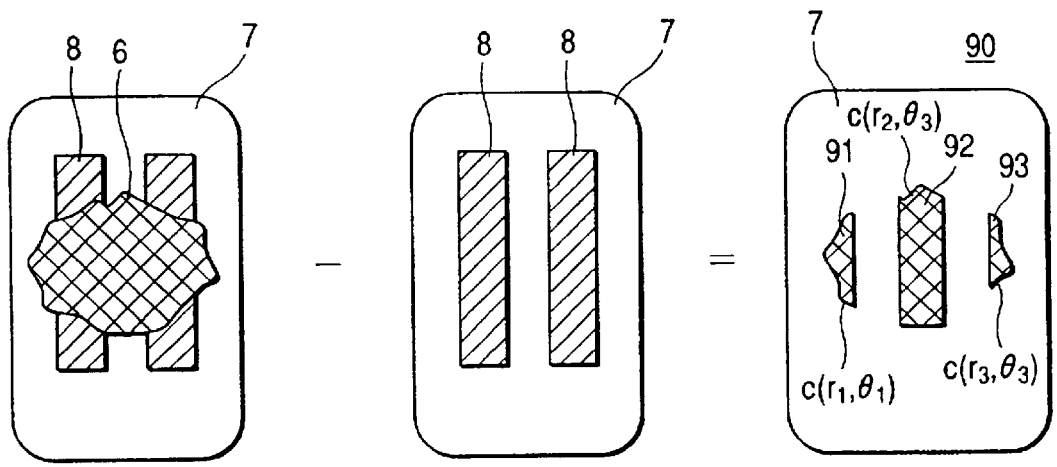
FIGS. 15(a) through (d) show views for explaining an acknowledgment of a single foreign matter, in a first variation of the another embodiment of the present invention mentioned in the above, in particular, (a) through (c) respective images thereof and (d) a tint-hue distribution map.

An aspect in the present variation, differing from the another embodiment mentioned in the above, lies in the method of acknowledgment of the single foreign matter when the image of the foreign matter is divided by that of the wiring pattern. Namely, as shown in FIGS. 15(a), (b) and (c), the determination of color is made for the divided images through the process of the subtraction, when the difference image 90 is divided into three (3).

Figure 15D:
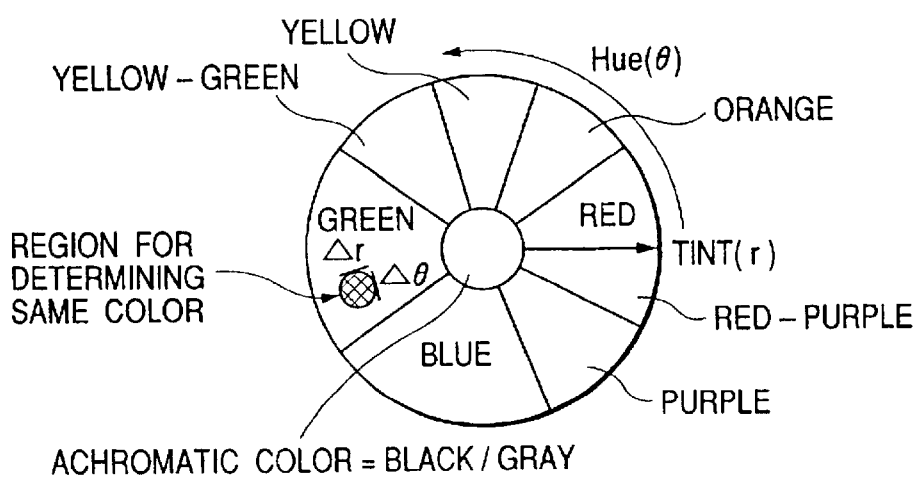

In a case where the image by means of the image pick-up device 45 is a color image which is outputted as NSTN (National Television System Committee) signal, the determination in the color is carried out by using a tint-hue distribution map shown in FIG. 15(d). When the left-hand side image 91, the central image 92 and the right-hand side image 93 are decided to be in the same color in a predetermined region of $\Delta\gamma$ and $\Delta\theta$, they are acknowledged to be the difference image 90 of the single foreign matter, then the measurement in the sizes of the foreign matter is carried out by combining them together as an unit and it is determined to be the killer defect. In a case where it is decided not in the same color, they are acknowledged to be the foreign matters separated to each other, and the measurement in the sizes are carried out for each of them. If the sizes of the foreign matter is larger than the distance between the patterns, then it is decided to be the killer defect, while if smaller, non-killer or not fatal defect.

In a case where the image by means of the image pick-up device 45 is a color image which is outputted as RGB signals, each color can be represented as below:

$$\Delta\alpha + \Delta\beta + \Delta\gamma$$

And, in a case where the following relationship is established, with respect to a predetermined value $\eta$, $$|\Delta\alpha| + |\Delta\beta| + |\Delta\gamma| \leq \eta$$

then, it is decided in the same color. If the divided images are decided to be in the same color in the above manner, they are acknowledged to be the foreign matter in the single body, and then the measurement in the diameter of the foreign matter is carried out by combining them together as an unit and it is determined to be the killer defect. In a case where it is decided not in the same color, they are acknowledged to be the foreign matters separated to each other, and the measurement in the sizes are carried out for each of them. If the sizes of the foreign matter is larger than the distance between the patterns, it is decided to be the killer defect, while if smaller, non-killer one.

As shown in FIG. 16, in a case where the number of division is two (2), the same process is carried out as in the case where the colors of the divided images are decided to be separated into three (3) colors mentioned above. If being decided to be in the same color, they are acknowledged to be the foreign matter in the single body, and then the measurement in the diameter of the foreign matter is carried out by combining them together as an unit, and this foreign matter is decided to be the possible defect. Further, the result of inspection is treated in the same manner as in the another embodiment mentioned above.

FIG. 17 is an view for explaining a function of acknowledgment of the single foreign matter in a second variation of the inspection method, according to the another embodiment of the present invention mentioned in the above.

An aspect in the present variation, differing from the another embodiment mentioned in the above, lies in the method of acknowledgment of the single foreign matter when the image of the foreign matter is divided by that of the wiring pattern. Namely, as shown in FIGS. 17(a), (b) and (c), the determination is made by an expansion process of the divided images.

As shown in FIG. 17, in a case that it is divided into the left-hand side image 91, the central image 92 and the right-hand side image 93, each element of those divided images is processed so as to be expanded by a value $\zeta$ which is inputted previously, as shown in FIG. 17(d). In the present variation, the value $\zeta$ is set at a value equal to the width of a space between the patterns. As a result of the expansion process, if the number of the images after the expansion process is less than that of originals, those divided elements are combined as an unit and are acknowledged to be the foreign matter in the single body. The measurement in the size of the foreign matter is carried out by measuring the distance between the left edge of the original left-hand side image 91 and the right edge of the right-hand side image 93, and the single foreign matter is decided as the killer defect. In a case where the number of the images after the expansion process is equal to that of the originals, those foreign matters in a group are acknowledged to be foreign matters being separate from each other to be decided as the possible defect. However, the result of inspection will be processed in the same manner as in the another embodiment mentioned above.

FIGS. 18(a) through (d) are views for explaining a function of acknowledgment of the single foreign matter in a third variation of the inspection method, according to the another embodiment of the present invention mentioned in the above.

An aspect in the present variation, differing from the another embodiment mentioned in the above, lies in the method of acknowledgment of the single foreign matter when the image of the foreign matter is divided by that of the wiring pattern. Namely, as shown in FIGS. 18(a), (b) and (c), the determination is made by use of a summation of images.

FIG. 18(a) shows the image of the object to be inspected at the coordinate position thereof, wherein a pair of wiring patterns 8 and 8 provided in parallel to each other appear on a background image 7, and the foreign matter 6 is in the condition that it appears to bridge over the both wiring patterns 8 and 8. FIG. 18(b) shows the image of the reference object at the coordinate position thereof, wherein only the both wiring patterns 8 and 8 appear on the background image 7. The image of the object to be inspected and the images of the wiring patterns 8 and 8 are summed up or added together so as to form the summation image 9' as shown in FIG. 18(c). Processing this summation image 9' with a threshold value, divided images 8' and 8' of the wiring patterns are formed from the foreign matter image 6 shown in FIG. 18(d). When are acknowledged such the images as divided in this manner, the foreign matter is decided to be the killer defect. If not acknowledged, it is decided to be the non-killer defect. Further, the inspection result is processed in the manner same to that in the another embodiment mentioned above.

In the above, although the invention made by inventors of the present inventions was explained in detail on the basis of the above embodiment and the variations thereof, however, it should not be restricted only to the embodiment and the variations thereof, and it is needless to say that it can be modified within a breadth without deviating beyond the gist of the invention.

For instance, the determination in the position of the foreign matter under the bright field illumination should not be restricted only with the-construction in which it is carried out by the optical shutter element, but it also can be carried out by such a construction that comparison of the data detected at the same position on the repeated patterns is done. In that case, the data to be compared with can be the detected data of the adjacent chip, a predetermined pattern which is memorized previously, or a standard pattern.

As the image pick-up device can be used not only that which uses the line sensor, but also that which uses the area sensor or an image pick-up tube, or the like.

In the above, there is mainly explained the invention which is made by the inventors, in particular, in a case where it is applied to a field of the foreign matter inspection technology for wafers as the background of the present invention, however, it should not be limited to this, and can be applied the whole of the inspection technology for a plate-like object in generally, including a photo mask or a liquid crystal panel, etc.

Finally, effects which can be obtained with the another embodiment and the variations thereof will be explained briefly as below.

Since the sizes of the foreign matter(s) is able to be outputted without using the apparatus which takes long time for inspection and/or a plurality units thereof, therefore the time length for inspecting per one (1) object can be shorten greatly. By judging whether the divided portions be the foreign matter in a single body or not so as to measuring the sizes thereof, it is possible to measure the sizes of the foreign matter(s) with accuracy all the more. By judging the fatality of the foreign matter (i.e., killer defect or not) from the pattern and the sizes and/or the property thereof, it is possible to rise up the efficiency of the method of inspection all the more.

By working out the rate of good chip product and the density of defects in a chip to be inspected, it is possible to rise up the efficiency in use of the inspection method all the more.

What is claimed:

1. A method for inspecting foreign matters in or on repeated micro-miniature patterns formed upon a surface of an object to be inspected, comprising the following steps:

illuminating an inspection light of dark field directed obliquely upon the surface of the object to be inspected, on which the repeated micro-miniature patterns are formed, with a dark field inspection light illuminating device;

detecting scattered light of the dark field inspection light being scattered from the surface of said object to be inspected with at least a scattered light detector;

determining a coordinate position of a foreign matter upon the surface of said object to be inspected, on a basis of the detection of said scattered light in the above step, and thereby generating position information of the foreign matter;

illuminating an inspection light of bright field directed perpendicularly upon the surface of the object to be inspected, on which the repeated micro-miniature patterns are formed, with a bright field inspection light illumination device;

picking up an image of said foreign matter whose coordinate position is determined in the above step, under the bright field illumination by the bright field inspection illuminating device for illuminating the bright field inspection light in the above step, when the coordinate of the bright field inspection light is coincident with the coordinate of said foreign matter;

deciding said foreign matter at least one of size, shape, color and property thereof, depending upon an image of said foreign matter which is extracted on a basis of the image picked up in the above step;

processing information relating to the foreign matters based on the deciding in said deciding step; and displaying said information relating to the foreign matters together with said coordinate position information of the foreign matter generated in said step of determining the coordinate position.

2. A method for inspecting foreign matters in or on repeated micro-miniature patterns, as defined in claim 1, further comprising a step of picking up an image of an another position of said repeated micro-miniature patterns of said object to be inspected, at a position corresponding to the coordinate position of said foreign matter which is determined by said detecting of the scattered light, under a bright field illumination by said illumination means, whereby the foreign matter image in said deciding step is extracted by comparing both said picked up images.

3. A method for inspecting foreign matters in or on repeated micro-miniature patterns, as defined in claim 1, further comprising a step of verifying appropriateness with respect to the determination made in said determining step of the coordinate position of said foreign matter upon the detecting of the scattered light, on a basis of the decision made on said foreign matter appearing in the image which is picked up in said picking up step.

4. A method for inspecting foreign matters in or on repeated micro-miniature patterns, as defined in claim 1, wherein the shape is determined in said deciding step, by use of the sizes of the image of said foreign matter which is obtained in said picking up step thereof.

5. A method for inspecting foreign matters in or on repeated micro-miniature patterns, as defined in claim 1, wherein the color is determined in said deciding step, by use of a color component and a gradation of the image of said foreign matter which is obtained in said picking up step thereof.

6. A method for inspecting foreign matters in or on repeated micro-miniature patterns, as defined in claim 1, wherein the property is determined in said deciding step, further by use of the scattered light from said detected foreign matter, which is detected with said scattered light detector.

7. An apparatus for inspecting foreign matters in or on repeated micro-miniature patterns formed upon a surface of an object to be inspected, comprising:

a dark field light illuminating device for illuminating a dark field inspection light directed obliquely upon the surface of the object to be inspected, on which the repeated micro-miniature patterns are formed;

a scattered light detector for detecting the scattered light of the dark field inspection light being scattered from the surface of said object to be inspected;

means for determining a coordinate position of a foreign matter upon the surface of said object to be inspected, on a basis of the detection of said scattered dark field light, and generating coordinate position information of the foreign matter;

an illumination means for applying a bright field illumination upon the surface of the object to be inspected, on which the repeated micro-miniature patterns are formed;

means for picking up an image of the foreign matter which is determined with the coordinate position thereof, under the bright field illumination by said illumination means, at the coordinate position corresponding to that which is determined through the scattered light detected by said scattered light detector under the dark field inspection light by said coordinate position determining means;

means for deciding the foreign matter at least one of size, shape, color and property thereof, depending upon an image of the foreign matter which is extracted on a basis of said picking up of the image obtained by said image picking up means;

means for processing information relating to the foreign matters based on the deciding of said means for deciding; and a display for displaying the processed information relating to the foreign matters together with said information of coordinate position of the foreign matters, which is generated by said coordinate position determining means.

8. An apparatus for inspecting foreign matters, as defined in claim 7, wherein said image picking up means and said scattered light detecting means are constructed for a common use thereof.

9. An apparatus for inspecting foreign matters, as defined in claim 7, wherein a stage, in which said image picking up means picks up the image under the bright field illumination by said illumination means, is provided separately from a stage in which said scattered light detector detects the scattered light under the inspection light from said light illuminating device.

10. An apparatus for inspecting foreign matters, as defined in claim 7, further including:

means for obtaining a reference image by picking up the image of the micro-miniature pattern, under a bright field illumination, at an another coordinate position on the surface of said object to be inspected, which is corresponding to but different from the coordinate position which is determined by said determining means; and means for obtaining an arithmetic processed image between said object image and said reference image, wherein said decision means decide a presence of a defect at the determined coordinate position on said object to be inspected, which is previously designated, on a basis of the arithmetic processed image obtained by said arithmetic processed image obtaining means.

11. An apparatus for inspecting foreign matters, as defined in claim 10, wherein said arithmetic processed image obtaining means obtain a difference image processed between said object image and said reference image.

12. An apparatus for inspecting foreign matters, as defined in claim 10, wherein said arithmetic processed image obtaining means obtain an addition image processed between said object image and said reference image.

* * * * *